(12) United States Patent
Blin et al.

(10) Patent No.: US 7,875,265 B2
(45) Date of Patent: *Jan. 25, 2011

(54) COSMETIC COMPOSITION COMPRISING A SEQUENCED POLYMER AND A PLASTICIZER

(75) Inventors: Xavier Blin, Paris (FR); Véronique Ferrari, Maisons-Alfort (FR)

(73) Assignee: L'Oreal, Paris (FR)

( * ) Notice: Subject to any disclaimer, the term of this patent is extended or adjusted under 35 U.S.C. 154(b) by 1411 days.

This patent is subject to a terminal disclaimer.

(21) Appl. No.: 10/529,318

(22) PCT Filed: Sep. 26, 2003

(86) PCT No.: PCT/FR03/02844

§ 371 (c)(1), (2), (4) Date: Mar. 25, 2005

(87) PCT Pub. No.: WO2004/028490

PCT Pub. Date: Apr. 8, 2004

(65) Prior Publication Data

US 2006/0134044 A1    Jun. 22, 2006

(30) Foreign Application Priority Data

Sep. 26, 2002  (FR)  .................................. 02 11949
Dec. 20, 2002  (FR)  .................................. 02 16437
May 21, 2003   (FR)  .................................. 03 06121

(51) Int. Cl.
A61K 31/74   (2006.01)
A61K 47/06   (2006.01)
A61Q 1/00    (2006.01)
A61Q 1/04    (2006.01)
A61Q 1/06    (2006.01)
A61Q 1/10    (2006.01)
A61Q 5/00    (2006.01)
A61Q 17/00   (2006.01)
A61Q 19/00   (2006.01)

(52) U.S. Cl. .............................. 424/64; 424/61; 424/63; 424/70.1; 424/70.11; 424/70.16; 424/70.19; 424/78.02; 424/78.03; 424/78.17; 424/78.18; 424/401; 514/844; 514/845; 514/937

(58) Field of Classification Search ................... 424/61, 424/63, 64, 70.1, 70.11, 70.16, 70.19, 78.02, 424/78.03, 78.17, 78.18, 401
See application file for complete search history.

(56) References Cited

U.S. PATENT DOCUMENTS

| | | |
|---|---|---|
| 2,047,398 A | 7/1936 | Voss et al. |
| 2,528,378 A | 10/1950 | Mannheimer et al. |
| 2,723,248 A | 11/1955 | Wright |
| 2,781,354 A | 2/1957 | Mannheimer et al. |
| 3,673,160 A | 6/1972 | Buisson et al. |
| 3,716,633 A | 2/1973 | Viout et al. |
| 3,802,841 A | 4/1974 | Robin |
| 3,836,537 A | 9/1974 | Boerwinkle et al. |
| 3,910,862 A | 10/1975 | Barabas et al. |
| 3,915,921 A | 10/1975 | Schlatzer et al. |
| 3,925,542 A | 12/1975 | Viout et al. |
| 3,937,811 A | 2/1976 | Papantoniou et al. |
| 3,946,749 A | 3/1976 | Papantoniou |
| 3,966,403 A | 6/1976 | Papantoniou et al. |
| 3,966,404 A | 6/1976 | Papantoniou et al. |
| 3,990,459 A | 11/1976 | Papantoniou |
| 4,030,512 A | 6/1977 | Papantoniou et al. |
| 4,031,307 A | 6/1977 | DeMartino et al. |
| 4,032,628 A | 6/1977 | Papantoniou et al. |
| 4,070,533 A | 1/1978 | Papantoniou et al. |
| 4,076,912 A | 2/1978 | Papantoniou et al. |
| RE29,871 E | 12/1978 | Papantoniou et al. |
| 4,128,631 A | 12/1978 | Lundmark et al. |
| 4,129,711 A | 12/1978 | Viout et al. |
| 4,131,576 A | 12/1978 | Iovine |
| 4,137,208 A | 1/1979 | Elliott |
| 4,152,416 A | 5/1979 | Spitzer et al. |
| 4,165,367 A | 8/1979 | Chakrabarti |

(Continued)

FOREIGN PATENT DOCUMENTS

DE      2 330 956      1/1974

(Continued)

OTHER PUBLICATIONS

HCAPLUS abstract 1964:70247, abstracting: Develop. Ind. Microbiol., vol. 2, pp. 47-53 (1961).*

(Continued)

*Primary Examiner*—John Pak
(74) *Attorney, Agent, or Firm*—Finnegan, Henderson, Farabow, Garrett & Dunner L.L.P.

(57) ABSTRACT

A subject matter of the invention is a cosmetic composition comprising a cosmetically acceptable organic liquid medium, a block polymer and a plasticizer, characterized in that:
the block polymer is a film-forming linear ethylenic polymer,
the plasticizer is a compound, the nature and the amount of which are such that the composition is capable of forming a film having a hardness of less than or equal to 35 seconds, the hardness of the film being measured using a Persoz pendulum according to Standard NF-T-30-016, and in particular a compound having a solubility parameter $\delta_h$ ranging from 5.5 to 11 $(J/cm^3)^{1/2}$.

Application to making-up and caring for keratinous substances, in particular the skin.

120 Claims, No Drawings

U.S. PATENT DOCUMENTS

| | | |
|---|---|---|
| 4,223,009 A | 9/1980 | Chakrabarti |
| 4,282,203 A | 8/1981 | Jacquet et al. |
| 4,289,752 A | 9/1981 | Mahieu et al. |
| 4,425,326 A | 1/1984 | Guillon et al. |
| 4,509,949 A | 4/1985 | Huang et al. |
| 4,693,935 A | 9/1987 | Mazurek |
| 4,728,571 A | 3/1988 | Clemens et al. |
| 4,887,622 A | 12/1989 | Gueret |
| 4,972,037 A | 11/1990 | Garbe et al. |
| 4,981,902 A | 1/1991 | Mitra et al. |
| 4,981,903 A | 1/1991 | Garbe et al. |
| 5,000,937 A | 3/1991 | Grollier et al. |
| 5,061,481 A | 10/1991 | Suzuki et al. |
| 5,110,582 A | 5/1992 | Hungerbuhler et al. |
| 5,156,911 A | 10/1992 | Stewart |
| 5,209,924 A | 5/1993 | Garbe et al. |
| 5,219,560 A | 6/1993 | Suzuki et al. |
| 5,266,321 A | 11/1993 | Shukuzaki |
| 5,362,485 A | 11/1994 | Hayama et al. |
| 5,391,631 A | 2/1995 | Porsch et al. |
| 5,468,477 A | 11/1995 | Kumar et al. |
| 5,472,798 A | 12/1995 | Kumazawa et al. |
| 5,492,426 A | 2/1996 | Gueret |
| 5,519,063 A | 5/1996 | Mondet et al. |
| 5,538,717 A | 7/1996 | De La Poterie |
| 5,681,877 A | 10/1997 | Hosotte-Filbert et al. |
| 5,686,067 A | 11/1997 | Shih et al. |
| 5,690,918 A | 11/1997 | Jacks et al. |
| 5,711,940 A | 1/1998 | Kuentz et al. |
| 5,725,882 A | 3/1998 | Kumar et al. |
| 5,736,125 A | 4/1998 | Morawsky et al. |
| 5,747,013 A | 5/1998 | Mougin et al. |
| 5,756,635 A | 5/1998 | Michaud et al. |
| 5,772,347 A | 6/1998 | Gueret |
| 5,783,657 A | 7/1998 | Pavlin et al. |
| 5,807,540 A | 9/1998 | Junino et al. |
| 5,849,275 A | 12/1998 | Calello et al. |
| 5,849,318 A | 12/1998 | Imai et al. |
| 5,879,095 A | 3/1999 | Gueret |
| 5,897,870 A | 4/1999 | Schehlmann et al. |
| 5,948,393 A | 9/1999 | Tomomasa et al. |
| 5,994,446 A | 11/1999 | Graulus et al. |
| 6,001,367 A | 12/1999 | Bazin et al. |
| 6,001,374 A | 12/1999 | Nichols |
| 6,027,739 A | 2/2000 | Nichols |
| 6,033,650 A | 3/2000 | Calello et al. |
| 6,059,473 A | 5/2000 | Gueret |
| 6,074,654 A | 6/2000 | Drechsler et al. |
| 6,083,516 A | 7/2000 | Curtis et al. |
| 6,106,813 A | 8/2000 | Mondet et al. |
| 6,106,820 A | 8/2000 | Morrissey et al. |
| 6,120,781 A | 9/2000 | Le Bras et al. |
| 6,126,929 A | 10/2000 | Mougin |
| 6,132,742 A | 10/2000 | Le Bras et al. |
| 6,139,849 A | 10/2000 | Lesaulnier et al. |
| 6,140,431 A | 10/2000 | Kinker et al. |
| 6,153,206 A | 11/2000 | Anton et al. |
| 6,156,804 A | 12/2000 | Chevalier et al. |
| 6,160,054 A | 12/2000 | Schwindeman et al. |
| 6,165,457 A | 12/2000 | Midha et al. |
| 6,166,093 A | 12/2000 | Mougin et al. |
| 6,174,968 B1 | 1/2001 | Hoxmeier |
| 6,180,123 B1 | 1/2001 | Mondet |
| 6,197,883 B1 | 3/2001 | Schimmel et al. |
| 6,225,390 B1 | 5/2001 | Hoxmeier |
| 6,228,946 B1 | 5/2001 | Kitayama et al. |
| 6,228,967 B1 | 5/2001 | Fost et al. |
| 6,238,679 B1 | 5/2001 | De La Poterie et al. |
| 6,254,878 B1 * | 7/2001 | Bednarek et al. ............ 424/401 |
| 6,258,916 B1 | 7/2001 | Michaud et al. |
| 6,267,951 B1 | 7/2001 | Shah et al. |
| 6,268,466 B1 | 7/2001 | MacQueen et al. |
| 6,280,713 B1 | 8/2001 | Tranchant et al. |
| 6,303,105 B1 | 10/2001 | Shah et al. |
| 6,319,959 B1 | 11/2001 | Mougin et al. |
| 6,326,011 B1 | 12/2001 | Miyazawa et al. |
| 6,328,495 B1 | 12/2001 | Gueret |
| 6,342,237 B1 | 1/2002 | Bara |
| 6,372,876 B1 | 4/2002 | Kim et al. |
| 6,386,781 B1 | 5/2002 | Gueret |
| 6,395,265 B1 | 5/2002 | Mougin et al. |
| 6,399,691 B1 | 6/2002 | Melchiors et al. |
| 6,410,005 B1 | 6/2002 | Galleguillos et al. |
| 6,410,666 B1 | 6/2002 | Grubbs et al. |
| 6,412,496 B1 | 7/2002 | Gueret |
| 6,423,306 B2 | 7/2002 | Caes et al. |
| 6,464,969 B2 | 10/2002 | De La Poterie et al. |
| 6,484,731 B1 | 11/2002 | Lacout |
| 6,491,927 B1 | 12/2002 | Arnaud et al. |
| 6,518,364 B2 | 2/2003 | Charmot et al. |
| 6,531,535 B2 | 3/2003 | Melchiors et al. |
| 6,552,146 B1 | 4/2003 | Mougin |
| 6,581,610 B1 | 6/2003 | Gueret |
| 6,649,173 B1 | 11/2003 | Arnaud et al. |
| 6,663,855 B2 | 12/2003 | Frechet et al. |
| 6,663,885 B1 | 12/2003 | Hager et al. |
| 6,685,925 B2 | 2/2004 | Frechet et al. |
| 6,692,173 B2 | 2/2004 | Gueret |
| 6,692,733 B1 | 2/2004 | Mougin |
| 6,770,271 B2 | 8/2004 | Mondet et al. |
| 6,805,872 B2 | 10/2004 | Mougin |
| 6,833,419 B2 | 12/2004 | Morschhauser et al. |
| 6,843,611 B2 | 1/2005 | Blondeel et al. |
| 6,866,046 B2 | 3/2005 | Gueret |
| 6,881,780 B2 | 4/2005 | Bryant et al. |
| 6,890,522 B2 | 5/2005 | Frechet et al. |
| 6,891,011 B2 | 5/2005 | Morschhauser et al. |
| 6,905,696 B2 * | 6/2005 | Marotta et al. ............... 424/401 |
| 6,946,518 B2 | 9/2005 | De La Poterie |
| 6,960,339 B1 | 11/2005 | Ferrari |
| 6,964,995 B2 | 11/2005 | Morschhauser et al. |
| 7,022,791 B2 | 4/2006 | Loffler et al. |
| 7,025,973 B2 | 4/2006 | Loffler et al. |
| 7,053,146 B2 | 5/2006 | Morschhauser et al. |
| 7,081,507 B2 | 7/2006 | Morschhauser et al. |
| 7,144,171 B2 | 12/2006 | Blondeel et al. |
| 7,151,137 B2 | 12/2006 | Morschhauser et al. |
| 7,176,170 B2 | 2/2007 | Dubief et al. |
| 7,186,405 B2 | 3/2007 | Loeffler et al. |
| 7,186,774 B2 | 3/2007 | Morschhauser et al. |
| 7,244,421 B2 | 7/2007 | Loffler et al. |
| 7,279,154 B2 | 10/2007 | Loffler et al. |
| 7,297,328 B2 | 11/2007 | Loffler et al. |
| 7,332,155 B2 | 2/2008 | Loffler et al. |
| 7,358,303 B2 | 4/2008 | De La Poterie |
| 7,393,520 B2 | 7/2008 | Loeffler et al. |
| 7,399,478 B2 | 7/2008 | Loffler et al. |
| 2002/0015611 A1 | 2/2002 | Blondeel et al. |
| 2002/0018759 A1 | 2/2002 | Pagano et al. |
| 2002/0020424 A1 | 2/2002 | Gueret |
| 2002/0035237 A1 | 3/2002 | Lawson et al. |
| 2002/0054783 A1 | 5/2002 | Gueret |
| 2002/0055562 A1 | 5/2002 | Butuc |
| 2002/0061319 A1 | 5/2002 | Bernard et al. |
| 2002/0064539 A1 * | 5/2002 | Philippe et al. ............. 424/401 |
| 2002/0076390 A1 | 6/2002 | Kantner et al. |
| 2002/0076425 A1 | 6/2002 | Mondet et al. |
| 2002/0098217 A1 | 7/2002 | Piot et al. |
| 2002/0115780 A1 | 8/2002 | Mougin |
| 2002/0150546 A1 | 10/2002 | Mougin et al. |
| 2002/0151638 A1 | 10/2002 | Melchiors et al. |
| 2002/0159965 A1 | 10/2002 | Frechet et al. |
| 2002/0160026 A1 | 10/2002 | Frechet et al. |
| 2003/0003154 A1 | 1/2003 | De La Poterie |

| | | | |
|---|---|---|---|
| 2003/0017124 A1 | 1/2003 | Agostini et al. | |
| 2003/0017182 A1 | 1/2003 | Tournilhac | |
| 2003/0021815 A9 | 1/2003 | Mondet et al. | |
| 2003/0024074 A1 | 2/2003 | Hartman | |
| 2003/0039621 A1 | 2/2003 | Arnaud et al. | |
| 2003/0059392 A1 | 3/2003 | L'Alloret | |
| 2003/0113285 A1 | 6/2003 | Meffert et al. | |
| 2003/0124074 A1 | 7/2003 | Mougin et al. | |
| 2003/0124079 A1 | 7/2003 | Mougin et al. | |
| 2003/0185774 A1 | 10/2003 | Dobbs et al. | |
| 2003/0191271 A1 | 10/2003 | Mondet et al. | |
| 2004/0009136 A1 | 1/2004 | Dubief et al. | |
| 2004/0013625 A1 | 1/2004 | Kanji | |
| 2004/0014872 A1 | 1/2004 | Raether | |
| 2004/0039101 A1 | 2/2004 | Dubief et al. | |
| 2004/0052745 A1 | 3/2004 | Bernard et al. | |
| 2004/0052752 A1 | 3/2004 | Samain et al. | |
| 2004/0077788 A1 | 4/2004 | Guerra et al. | |
| 2004/0091444 A1 | 5/2004 | Loeffler et al. | |
| 2004/0093676 A1 | 5/2004 | Vidal et al. | |
| 2004/0096409 A1 | 5/2004 | Loeffler et al. | |
| 2004/0096411 A1 | 5/2004 | Frechet et al. | |
| 2004/0097657 A1 | 5/2004 | Morschhauser et al. | |
| 2004/0109835 A1 | 6/2004 | Loffler et al. | |
| 2004/0109836 A1 | 6/2004 | Loffler et al. | |
| 2004/0109838 A1 | 6/2004 | Morschhauser et al. | |
| 2004/0115148 A1 | 6/2004 | Loffler et al. | |
| 2004/0115149 A1 | 6/2004 | Loffler et al. | |
| 2004/0115157 A1 | 6/2004 | Loffler et al. | |
| 2004/0116628 A1 | 6/2004 | Morschhauser et al. | |
| 2004/0116634 A1 | 6/2004 | Morschhauser et al. | |
| 2004/0120906 A1 | 6/2004 | Toumi et al. | |
| 2004/0120920 A1 | 6/2004 | Lion et al. | |
| 2004/0137020 A1 | 7/2004 | De La Poterie et al. | |
| 2004/0137021 A1 | 7/2004 | De La Poterie et al. | |
| 2004/0141937 A1 | 7/2004 | Loffler et al. | |
| 2004/0141943 A1 | 7/2004 | Mougin et al. | |
| 2004/0142831 A1 | 7/2004 | Jager Lezer | |
| 2004/0167304 A1 | 8/2004 | Morschhauser et al. | |
| 2004/0223933 A1 | 11/2004 | Hiwatashi et al. | |
| 2004/0241118 A1 | 12/2004 | Simon et al. | |
| 2005/0002724 A1 | 1/2005 | Blondeel et al. | |
| 2005/0020779 A1 | 1/2005 | Mougin et al. | |
| 2005/0032998 A1 | 2/2005 | Morschhauser et al. | |
| 2005/0089536 A1 | 4/2005 | Loffler et al. | |
| 2005/0095213 A1* | 5/2005 | Blin et al. | 424/70.11 |
| 2005/0106197 A1 | 5/2005 | Blin et al. | |
| 2005/0129641 A1 | 6/2005 | Arnaud et al. | |
| 2005/0201958 A1 | 9/2005 | De La Poterie | |
| 2005/0220747 A1 | 10/2005 | Lion et al. | |
| 2005/0232887 A1 | 10/2005 | Morschhauser et al. | |
| 2005/0287103 A1 | 12/2005 | Filippi et al. | |
| 2006/0093568 A1* | 5/2006 | Blin et al. | 424/70.16 |
| 2006/0099164 A1* | 5/2006 | De La Poterie et al. | 424/70.1 |
| 2006/0099231 A1 | 5/2006 | De La Poterie et al. | |
| 2006/0115444 A1* | 6/2006 | Blin et al. | 424/70.16 |
| 2006/0127334 A1 | 6/2006 | Ferrari et al. | |
| 2006/0134032 A1* | 6/2006 | Ilekti et al. | 424/61 |
| 2006/0134038 A1 | 6/2006 | De La Poterie et al. | |
| 2006/0134044 A1 | 6/2006 | Blin et al. | |
| 2006/0134051 A1* | 6/2006 | Blin et al. | 424/70.16 |
| 2006/0147402 A1* | 7/2006 | Blin et al. | 424/70.16 |
| 2006/0147403 A1 | 7/2006 | Ferrari et al. | |
| 2007/0003506 A1 | 1/2007 | Mougin et al. | |
| 2007/0003507 A1 | 1/2007 | Mougin et al. | |
| 2007/0166259 A1 | 7/2007 | Vicic et al. | |
| 2008/0014232 A1 | 1/2008 | Arnaud et al. | |
| 2008/0050329 A1* | 2/2008 | De La Poterie | 424/70.7 |
| 2008/0069793 A1 | 3/2008 | Loffler et al. | |
| 2008/0107617 A1 | 5/2008 | Loffler et al. | |
| 2008/0159965 A1 | 7/2008 | Mougin et al. | |
| 2008/0207773 A1 | 8/2008 | Loffler et al. | |
| 2008/0219943 A1* | 9/2008 | De La Poterie | 424/70.7 |

FOREIGN PATENT DOCUMENTS

| | | |
|---|---|---|
| DE | 100 22 247 | 11/2001 |
| DE | 100 29 697 | 12/2001 |
| EP | 1 279 398 | 9/1971 |
| EP | 0 080 976 | 6/1983 |
| EP | 0 173 09 | 3/1986 |
| EP | 0 216 479 | 4/1987 |
| EP | 0 295 886 | 12/1988 |
| EP | 0 320 218 | 6/1989 |
| EP | 0 388 582 | 9/1990 |
| EP | 0 412 704 | 2/1991 |
| EP | 0 412 707 | 2/1991 |
| EP | 0 549 494 | 6/1993 |
| EP | 0 582 152 | 2/1994 |
| EP | 0 619 111 | 10/1994 |
| EP | 0 637 600 | 2/1995 |
| EP | 0 648 485 | 4/1995 |
| EP | 0 656 021 | 6/1995 |
| EP | 0 667 146 | 8/1995 |
| EP | 0 550 745 | 9/1995 |
| EP | 0 686 858 | 12/1995 |
| EP | 0 750 031 | 12/1996 |
| EP | 0 751 162 | 1/1997 |
| EP | 0 751 170 | 1/1997 |
| EP | 0 815 836 | 1/1998 |
| EP | 0 847 752 | 6/1998 |
| EP | 0 861 859 | 9/1998 |
| EP | 0 951 897 | 10/1999 |
| EP | 0 955 039 | 11/1999 |
| EP | 1 018 311 | 7/2000 |
| EP | 1 024 184 | 8/2000 |
| EP | 1 043 345 | 10/2000 |
| EP | 1 066 817 | 1/2001 |
| EP | 1 068 856 | 1/2001 |
| EP | 1 082 953 | 3/2001 |
| EP | 1 159 950 | 12/2001 |
| EP | 1 192 930 | 4/2002 |
| EP | 1 201 221 | 5/2002 |
| EP | 1 356 799 | 10/2003 |
| EP | 1 366 741 | 12/2003 |
| EP | 1 366 744 | 12/2003 |
| EP | 1 366 746 | 12/2003 |
| EP | 1 411 069 A2 | 4/2004 |
| EP | 1 421 928 A2 | 5/2004 |
| EP | 1 440 680 A1 | 7/2004 |
| EP | 1 518 534 | 3/2005 |
| EP | 1 518 535 | 3/2005 |
| EP | 1 604 634 | 12/2005 |
| FR | 1 222 944 | 6/1960 |
| FR | 1 400 366 | 4/1965 |
| FR | 1 564 110 | 3/1969 |
| FR | 1 580 545 | 9/1969 |
| FR | 2 077 143 | 9/1971 |
| FR | 2 079 785 | 11/1971 |
| FR | 2 140 977 | 1/1973 |
| FR | 2 232 303 | 1/1975 |
| FR | 2 265 781 | 10/1975 |
| FR | 2 265 782 | 10/1975 |
| FR | 2 350 384 | 12/1977 |
| FR | 2 357 241 | 2/1978 |
| FR | 2 393 573 | 1/1979 |
| FR | 2 439 798 | 5/1980 |
| FR | 2 710 552 | 4/1995 |
| FR | 2 710 646 | 4/1995 |
| FR | 2 722 380 | 1/1996 |
| FR | 2 727 609 | 6/1996 |
| FR | 2 743 297 | 7/1997 |
| FR | 2 761 959 | 10/1998 |
| FR | 2 775 566 | 9/1999 |
| FR | 2 775 593 | 9/1999 |

| | | |
|---|---|---|
| FR | 2 791 042 | 9/2000 |
| FR | 2 791 987 | 10/2000 |
| FR | 2 791 988 A1 | 10/2000 |
| FR | 2 792 190 | 10/2000 |
| FR | 2 792 618 | 10/2000 |
| FR | 2 796 529 | 1/2001 |
| FR | 2 798 061 | 3/2001 |
| FR | 2 803 743 | 7/2001 |
| FR | 2 806 273 | 9/2001 |
| FR | 2 296 402 | 11/2001 |
| FR | 2 809 306 | 11/2001 |
| FR | 2 811 993 | 1/2002 |
| FR | 2 814 365 | 3/2002 |
| FR | 2 816 503 | 5/2002 |
| FR | 2 823 101 | 10/2002 |
| FR | 2 823 103 | 10/2002 |
| FR | 2 827 514 A1 | 1/2003 |
| FR | 2 831 430 | 5/2003 |
| FR | 2 832 719 | 5/2003 |
| FR | 2 832 720 | 5/2003 |
| FR | 2 834 458 | 7/2003 |
| FR | 2 840 205 A1 | 12/2003 |
| FR | 2 840 209 A1 | 12/2003 |
| FR | 2 842 417 | 1/2004 |
| FR | 2 844 709 | 3/2004 |
| FR | 2 860 143 A1 | 4/2005 |
| FR | 2 860 156 A1 | 4/2005 |
| FR | 2 880 268 | 7/2006 |
| GB | 0 839 805 | 6/1960 |
| GB | 0 922 457 | 4/1963 |
| GB | 1 021 400 | 3/1966 |
| GB | 1 169 862 | 11/1969 |
| GB | 1 324 745 | 7/1973 |
| GB | 1 331 819 | 9/1973 |
| GB | 1 407 659 | 9/1975 |
| GB | 1 572 626 | 7/1980 |
| JP | 5-221829 | 8/1993 |
| JP | 06-279323 | 10/1994 |
| JP | 07-196450 | 8/1995 |
| JP | 07-309721 | 11/1995 |
| JP | 07-324017 | 12/1995 |
| JP | 10-506404 | 4/1996 |
| JP | 08-119836 | 5/1996 |
| JP | 09-263518 | 10/1997 |
| JP | H11-100307 | 4/1999 |
| JP | 11-124312 | 5/1999 |
| JP | 2000-83728 | 3/2000 |
| JP | 2000-319325 | 11/2000 |
| JP | 2000-319326 | 11/2000 |
| JP | 2001-348553 | 12/2001 |
| JP | 2001-527559 | 12/2001 |
| JP | 2002-201110 | 7/2002 |
| JP | 2002-201244 | 7/2002 |
| JP | 2003-40336 | 2/2003 |
| JP | 2003-73222 | 3/2003 |
| JP | 2003-081742 | 3/2003 |
| JP | 2003-286142 | 10/2003 |
| JP | 2004-2432 | 1/2004 |
| JP | 2004-2435 | 1/2004 |
| JP | 2004-149772 | 5/2004 |
| JP | 2004-269497 | 9/2004 |
| JP | 2005/104979 | 4/2005 |
| JP | 2006-503921 | 2/2006 |
| JP | 2006-507355 | 3/2006 |
| JP | 2006-507365 | 3/2006 |
| JP | 2006-507366 | 3/2006 |
| JP | 2006-507367 | 3/2006 |
| JP | 2006-151867 | 6/2006 |
| LU | 75370 | 7/1976 |
| LU | 75371 | 7/1976 |
| WO | WO 93/01797 | 2/1993 |
| WO | WO 93/23009 | 11/1993 |
| WO | WO 93/23446 | 11/1993 |
| WO | WO 94/03510 | 2/1994 |
| WO | WO 95/00578 | 1/1995 |
| WO | WO 95/03776 | 2/1995 |
| WO | WO 95/06078 | 3/1995 |
| WO | WO 96/10044 | 4/1996 |
| WO | WO 97/17057 | 5/1997 |
| WO | WO 98/31329 | 7/1998 |
| WO | WO 98/38981 | 9/1998 |
| WO | WO 98/42298 | 10/1998 |
| WO | WO 98/44012 | 10/1998 |
| WO | WO 98/51276 A1 | 11/1998 |
| WO | WO 00/26285 | 5/2000 |
| WO | WO 00/28948 | 5/2000 |
| WO | WO 00/40216 | 7/2000 |
| WO | WO 00/49997 | 8/2000 |
| WO | WO 01/03538 | 1/2001 |
| WO | WO 01/13863 | 3/2001 |
| WO | WO 01/19333 | 3/2001 |
| WO | WO 01/30886 | 5/2001 |
| WO | WO 01/43703 A1 | 6/2001 |
| WO | WO 01/51018 | 7/2001 |
| WO | WO 01/89470 A1 | 11/2001 |
| WO | WO 01/95871 | 12/2001 |
| WO | WO 02/05762 | 1/2002 |
| WO | WO 02/05765 | 1/2002 |
| WO | WO 02/28358 A1 | 4/2002 |
| WO | WO 02/34218 | 5/2002 |
| WO | WO 02/067877 | 9/2002 |
| WO | WO 02/080869 | 10/2002 |
| WO | WO 03/018423 | 3/2003 |
| WO | WO 03/046032 | 6/2003 |
| WO | WO 03/046033 | 6/2003 |
| WO | WO 2004/022009 | 3/2004 |
| WO | WO 2004/022010 | 3/2004 |
| WO | WO 2004/024700 A1 | 3/2004 |
| WO | WO 2004/028485 A2 | 4/2004 |
| WO | WO 2004/028487 A2 | 4/2004 |
| WO | WO 2004/028489 | 4/2004 |
| WO | WO 2004/028491 A2 | 4/2004 |
| WO | WO 2005/030158 A1 | 4/2005 |

OTHER PUBLICATIONS

Flick, Ernest W. Cosmetics Additives. An Industrial Guide. Noyes Publications, Park Ridge, NJ, p. 266 (1991).*
Co-pending U.S. Appl. No. 10/528,698, filed Mar. 22, 2005; Inventors: Veronique Ferrari et al.
Co-pending U.S. Appl. No. 10/528,835, filed Mar. 23, 2005; Inventors: Xavier Blin et al.
Co-pending U.S. Appl. No. 10/529,218, filed Mar. 25, 2005; Inventors: Xavier Blin et al.
Co-pending U.S. Appl. No. 10/670,388, filed Sep. 26, 2003; Inventors: Beatrice Toumi et al.
Co-pending U.S. Appl. No. 10/670,478, filed Sep. 26, 2003; Inventors: Bertrand Lion et al.
Co-pending U.S. Appl. No. 11/858,994, filed Sep. 21, 2007; Inventors: Bertrand Lion et al.
Co-pending U.S. Appl. No. 11/859,004, filed Sep. 21, 2007; Inventors: Bertrand Lion et al.
Co-pending U.S. Appl. No. 11/859,015, filed Sep. 21, 2007; Inventors: Bertrand Lion et al.
English language Abstract of FR 2 710 552, dated Apr. 7, 1995.
English language Abstract of FR 2 710 646, dated Apr. 7, 1995.
English language Abstract of FR 2 791 987, dated Oct. 13, 2000.
English language Abstract of FR 2 832 720, dated May 30, 2003.
English language Abstract of JP 07-309721, dated Nov. 28, 1995.
English language Abstract of JP 08-119836, dated May 14, 1996.
English language Abstract of WO 01/13863, dated Mar. 1, 2001.
English language Abstract of WO 01/51018, dated Jul. 19, 2001.
English language Derwent Abstract of DE 100 29 697, dated Dec. 20, 2001.
Boutevin, B. et al., "Study of Morphological and Mechanical Properties of PP/PBT," Polymer Bulletin, 34, pp. 117-123, (1995).

Buzin, A. et al., "Calorimetric Study of Block-Copolymers of Poly(n-butyl Acrylate) and Gradient Poly(n-butyl acrylate-co-methyl methacrylate)" vol. 43, 2002, pp. 5563-5569.
Co-pending U.S. Appl. No. 10/529,265, filed Sep. 28, 2005; Inventors: Xavier Blin et al.
Co-pending U.S. Appl. No. 10/529,267, filed Sep. 29, 2005; Inventors: Valerie De La Poterie et al.
Co-pending U.S. Appl. No. 10/585,817, filed Jan. 10, 2007; Inventor: Valerie De La Poterie.
Co-pending U.S. Appl. No. 10/585,818, filed Jul. 12, 2006; Inventors: Valerie De La Poterie.
Co-pending U.S. Appl. No. 10/949,448, filed Sep. 27, 2004; Inventors: Xavier Blin et al.
English language Derwent Abstract for EP 0 080 976, dated Jun. 8, 1983.
English language Derwent Abstract for FR 2 792 190, dated Oct. 20, 2000.
English language Derwent Abstract for FR 2 831 430, dated May 2, 2003.
English language Derwent Abstract for JP 06-279323, dated Oct. 4, 1994.
English language Derwent Abstract for JP 07-196450, dated Aug. 1, 1995.
English language Derwent Abstract for JP 09-263518, dated Oct. 7, 1997.
English language Derwent Abstract of JP 5-221829, dated Aug. 31, 1993.
French Search Report for FR 03/11340 for Copending U.S. Appl. No. 10/949,448, dated May 9, 2005.
Hamley, I.W., "Crystallization in Block Copolymers," Advances in Polymer Science, vol. 148, pp. 113-137 (1999).
International Search Report for PCT Application No. PCT/FR03/02849, dated Jun. 24, 2004.
International Search Report for PCT/FR03/02841, dated Jun. 1, 2004.
International Search Report for PCT/IB2005/000230, dated May 27, 2005.
International Search Report for PCT/IB2005/000236, dated Aug. 3, 2005.
Kirk-Othmer, "Encyclopedia of Chemical Technology", vol. 22, 3rd Edition, Wiley, 1979, pp. 333-432.
Nojima. S., "Melting Behavior of Poly (E-caprolactone)-block-polybutadiene Copolymers", Macromolecules, 32, 3727-3734 (1999).
Office Action mailed Dec. 10, 2008, in co-pending U.S. Appl. No. 10/528,698.
Office Action mailed Dec. 23, 2008, in co-pending U.S. Appl. No. 10/529,266.
Office Action mailed Nov. 25, 2008, in co-pending U.S. Appl. No. 10/949,448.
Prince, L.M. ed., Macroemulsions Theory and Practice, Academic Press (1977), pp. 21-32.
Rangarajan P., et al., "Morphology of Seni-Crystalline Block Copolymers of Ethylene-(ethylene-alt-propylene)," Macromolecules, 26, 4640-4645 (1993).
Richter, P. et al., "Polymer Aggregates with Crystalline Cores: The System Poly(ethylene)-poly(ethylene-propylene)," Macromolecules, 30, 1053-1068 (1997).
Thermal_Transisitons_of_Homopolymers.pdf. Thermal Transistions of Homopolymers: Glass Transistion & Melting Point Data. Accessed online Dec. 19, 2008 at: http://www.sigmaaldrich.com/etc/medialib/docs/Aldrich/General_Information/thermal_transitions_of_homopolymers.Par.0001.File.tmp/thermal_transitions_of_homopolymers.pdf.
Aldrich: Polymer Properties; 4th Ed. Catalog No. Z41, 247-3 (1999) published by John Wiley, New York.
Co-pending U.S. Appl. No. 10/573,579; filed Dec. 26, 2006; Inventor: Marco Vicic et al.
Co-pending U.S. Appl. No. 11/086,906, filed Mar. 23, 2005; Inventors: Philippe Ilekti et al.
Co-pending U.S. Appl. No. 11/089,210, filed Mar. 25, 2005.
English language Abstract of FR 2 834 458, dated Jul. 11, 2003.
English language Derwent Abstract for FR 2 775 566, dated Sep. 10, 1999.
English language Derwent Abstract for JP 11-124312, dated May 11, 1999.
Fonnum, et al., "Associative Thickeners. Part I: Synthesis, Rheology and Aggregation Behavior", Colloid Polym. Sci., 1993, 271: 380-389.
French Search Report for FR 04/03090, dated Sep. 30, 2004.
French Search Report for FR 04/50572, for Copending U.S. Appl. No. 11/086,906, dated Nov. 9, 2004.
Office Action mailed Aug. 12, 2009 in co-pending U.S. Appl. No. 10/949,448.
Office Action mailed Aug. 18, 2009 in co-pending U.S. Appl. No. 10/529,264.
Office Action mailed Jun. 12, 2009 in co-pending U.S. Appl. No. 11/086,906.
Office Action mailed Jun. 24, 2009 in co-pending U.S. Appl. No. 10/528,698.
Office Action mailed Jun. 24, 2009 in co-pending U.S. Appl. No. 10/529,267.
Office Action mailed Jun. 29, 2009 in co-pending U.S. Appl. No. 10/529,266.
Office Action mailed Jun. 4, 2009 in co-pending U.S. Appl. No. 10/670,478.
Office Action mailed Jun. 8, 2009 in co-pending U.S. Appl. No. 11/089,210.
Office Action mailed Mar. 12, 2009, in co-pending U.S. Appl. No. 10/529,218.
Office Action mailed Mar. 18, 2009, in co-pending U.S. Appl. No. 10/528,699.
Office Action mailed Mar. 18, 2009, in co-pending U.S. Appl. No. 10/573,579.
Office Action mailed Oct. 27, 2009 in co-pending U.S. Appl. No. 10/529,218.
Office Action mailed Sep. 28, 2009 in co-pending U.S. Appl. No. 10/670,478.
Porter, "Chapter 7: Non Ionics," Handbook of Surfactants, 1991, pp. 116-178, Chapman and Hall, New York.
Co-pending U.S. Appl. No. 10/949,435, filed Sep. 27, 2004; Inventors: Xavier Blin et al.
Co-pending U.S. Appl. No. 11/878,067, filed Jul. 20, 2007; Inventors: Caroline Lebre et al.
Co-pending U.S. Appl. No. 11/878,849, filed Jul. 27, 2007; Inventors: Celine Farcet et al.
Cortazar, M. et al., "Glass Transition Temperatures of Plasticized Polyarylate,", Polymer Bulletin 18, 149-154 (1987).
English language Abstract of EP 1 518 535, dated Mar. 30, 2005.
English language Abstract of EP 1 604 634, dated Dec. 14, 2005.
English language Abstract of FR 1 222 944, dated Jun. 14, 1960.
English language Abstract of FR 1 564 110, dated Jan. 1968.
English language Abstract of FR 2 357 241, dated Feb. 3, 1978.
English language Abstract of FR 2 880 268, dated Jul. 7, 2006.
English language Abstract of JP 2003-40336, Feb. 13, 2003.
English language Abstract of JP 2006-151867, dated Jun. 15, 2006.
Erichsen, J. et al., "Molecular Weight Dependence of the Surface Glass Transition of Polystyrene Films Investigated by the Embedding of Gold Nanoclusters," MRS Publication, 2001.
French Search Report for FR 04/03088, dated Nov. 2, 2004.
French Search Report for FR 06/53144, dated Feb. 13, 2007.
French Search Report for FR 06/53154, dated Apr. 2, 2007.
Nojiri, A. et al., "Molecular Weight Dependence of the Glass Transition Temperature in Poly(vinyl acetate)," Japan J. Appl. Phys. 10 (1971), p. 803.
Office Action mailed Apr. 28, 2010, in co-pending U.S. Appl. No. 10/528,835.
Office Action mailed Dec. 29, 2009, in co-pending U.S. Appl. No. 10/529,265.
Office Action mailed Dec. 3, 2009 in co-pending U.S. Appl. No. 10/528,698.
Office Action mailed Feb. 2, 2010, in co-pending U.S. Appl. No. 10/949,448.
Office Action mailed Feb. 27, 2009, in co-pending U.S. Appl. No. 11/878,849.

Office Action mailed Jan. 28, 2010, in co-pending U.S. Appl. No. 10/529,264.
Office Action mailed Jul. 21, 2009, in co-pending U.S. Appl. No. 11/878,067.
Office Action mailed Mar. 18, 2009, in related U.S. Appl. No. 11/089,172.
Office Action mailed Mar. 30, 2010, in co-pending U.S. Appl. No. 11/089,210.
Office Action mailed Mar. 30, 2010, in co-pending U.S. Appl. No. 11/878,067.
Office Action mailed May 12, 2010, in co-pending U.S. Appl. No. 11/086,906.
Office Action mailed Nov. 17, 2009 in co-pending U.S. Appl. No. 10/528,835.
Office Action mailed Nov. 6, 2009 in co-pending U.S. Appl. No. 10/949,435.
Office Action mailed Sep. 9, 2009, in co-pending U.S. Appl. No. 11/878,849.
Related U.S. Appl. No. 11/089,172, filed Mar. 25, 2005, Inventors: Katarina Benabdillah et al.
Specific Gravity and Viscosity of Liquid Table; available at http://www.csgnetwork.com/sgvisc.html. Sesame seed oil information originally published Mar. 28, 2002.
Toniu, P. et al., "Process for Preparation of Block Polymers, Products Obtained by Means of the Process and Cosmetic Compositions Containing Them", 1973, French Patent Office, pp. 1-26 (English translation of French Patent No. FR2140977).
Co-pending U.S. Appl. No. 10/528,699, filed Mar. 22, 2005; Inventors: Philippe Ilekti et al.
Co-pending U.S. Appl. No. 10/529,264, filed Mar. 25, 2005; Inventors: Veronique Ferrari et al.
Co-pending U.S. Appl. No. 10/529,266, filed Mar. 25, 2005; Inventors: Xavier Blin et al.
English Derwent Abstract for EP 1 082 953, (2001).
English Derwent Abstract for EP 1 159 950, (2001).
English Derwent Abstract for FR 2 798 061, (2001).
English Derwent Abstract for FR 2 832 719, (2003).
English Derwent Abstract for FR 2 803 743, (2001).
English Derwent Abstract for WO 01/03538, (2001).
English Derwent Abstract for WO 04/028489, (2004).
International Search Report for PCT/FR03/002844 (Priority Application for U.S. Appl. No. 10/529,318), dated May 14, 2005.
International Search Report for PCT/FR03/002847 (Priority Application for U.S. Appl. No. 10/529,266), dated May 17, 2004.
International Search Report for PCT/FR03/02842 (Priority Application for U.S. Appl. No. 10/529,218), dated May 17, 2004.
International Search Report for PCT/FR03/02845 (Priority Application for U.S. Appl. No. 10/529,264), dated May 17, 2004.
International Search Report for PCT/FR03/02848 (Priority Application for U.S. Appl. No. 10/528,835), dated May 17, 2004.
International Search Report for PCT/FR03/02846 (Priority Application for U.S. Appl. No. 10/528,699), dated May 17, 2004.
International Search Report for PCT/FR03/02843 (Priority Application for U.S. Appl. No. 10/528,698), dated May 17, 2004.
Derwent Abstract of FR 2 860 156, (2005).
Derwent Abstract of JP 2001/348553, (2001).
Derwent Abstract of JP H11-100307, (1999).
Dement Abstrdct of JP 2004/002435, (2004).
Derwent Abstract of JP 2004/002432, (2004).
English language Derwent Abstract of EP 0 648 485, dated Apr. 19, 1995.
English language Derwent Abstract of FR 2 140 977, dated Jan. 19, 1973.
English language Derwent Abstract of JP 2002-201244, dated Jul. 19, 2002.
European Search Report for EP 03 292 383, dated May 17, 2004, in Co-pending U.S. Appl. No. 10/670,388.
French Search Report for FR 02/11949 for Copending U.S. Appl. No. 10/670,478, dated Jul. 7, 2003.
Hansen, C.M., "The Three Dimensional Solubility Parameter—Key to Paint Component Affinities: I. Solvents, Plasticizers, Polymers, and Resins", Journal of Paint Technology, vol. 39, No. 505, pp. 104-117 (1967).
Machine Translation of JP 2002-201244, (2002).
Office Action mailed Aug. 12, 2005, in co-pending U.S. Appl. No. 10/670,478.
Office Action mailed Jan. 7, 2008, in co-pending U.S. Appl. No. 10/670,388.
Office Action mailed Mar. 26, 2008, in co-pending U.S. Appl. No. 10/670,478.
Office Action mailed Mar. 7, 2006, in co-pending U.S. Appl. No. 10/670,478.
Office Action mailed May 3, 2007, in co-pending U.S. Appl. No. 10/670,478.
Office Action mailed Nov. 15, 2006, in co-pending U.S. Appl. No. 10/670,478.
Office Action mailed Nov. 25, 2008, in co-pending U.S. Appl. No. 10/670,388.
Office Action mailed Oct. 21, 2008, in co-pending U.S. Appl. No. 10/670,478.
Office Action mailed Sep. 7, 2007, in co-pending U.S. Appl. No. 10/670,478.
Pigeon, R. et al., Chimie Macromoleculaire Appliquee, No. 600, 40/41; pp. 139-158, (1974), Abstract.

* cited by examiner

COSMETIC COMPOSITION COMPRISING A SEQUENCED POLYMER AND A PLASTICIZER

A subject matter of the present invention is a cosmetic composition comprising a specific block polymer and a specific plasticizer which is intended to be applied to human keratinous substances, such as the skin, lips, eyelashes, eyebrows, nails or hair. The composition is more particularly intended to be applied to the skin or lips.

The composition according to the invention can be a composition for making up or a composition for caring for keratinous substances, in particular the skin and lips, and preferably a makeup composition.

The makeup composition can be a product for making up the lips (lipstick), a foundation, an eyeshadow, a blusher, a concealer, an eyeliner, a product for making up the body, a mascara, a nail varnish or a product for making up the hair.

The care composition can be a product for caring for the skin of the body and of the face, in particular an antisun product or product for coloring the skin (such as a self-tanning product). The composition can also be a hair product, in particular for the form retention of the hairstyle or the shaping of the hair.

Lipstick and foundation compositions are commonly employed to give an attractive color to the lips or skin, in particular to the face. These makeup products generally comprise fatty phases, such as waxes and oils, pigments and/or fillers and optionally additives, such as cosmetic or dermatological active principles.

These compositions, when they are applied to the skin, exhibit the disadvantage of transferring, that is to say of being at least partially deposited and leaving traces on certain substrates with which they may be brought into contact, in particular a glass, a cup, a cigarette, an item of clothing or the skin. This results in a mediocre hold of the applied film, requiring the regular renewal of the application of the foundation or lipstick composition. Furthermore, the appearance of these unacceptable traces, in particular on blouse collars, can dissuade some women from using this type of makeup.

Advantageously "transfer-free" compositions for making up keratinous substances, in particular the lips and skin, are therefore sought which exhibit the advantage of forming a deposited layer possessing good hold, in particular which is not deposited, at least in part, on the substrates with which they are brought into contact (glass, items of clothing, cigarette, fabrics).

The use of film-forming polymers for improving the hold of makeup products is known. For example, the documents U.S. Pat. No. 6,074,654 and WO 02/067877 provide for the use of silicone resins.

However, the introduction of these film-forming polymers can result in excessively hard films which then have a tendency to crack over time. In particular, these hard films do not correctly follow the movement of the skin or lips and thus exhibit poor hold on the skin or lips, the film rapidly disintegrating.

Furthermore, an excessively hard film deposited on the lips or skin will bring about a feeling of tightness, rendering the deposited layer uncomfortable to the user.

One aim of the present invention is thus to provide a cosmetic composition capable of forming a flexible film capable in particular of following the movements of the lips or skin.

Another aim of the invention is to provide a cosmetic composition forming a deposited layer on keratinous substances, in particular on the skin or lips, which is comfortable all the time.

The inventors have discovered that it is possible to obtain such a composition by using a specific block polymer in combination with a specific plasticizer.

More specifically, a subject matter of the present invention is thus a cosmetic composition, in particular for making up or caring for keratinous substances, especially the skin or lips, comprising a cosmetically acceptable organic liquid medium, a block polymer and a plasticizer, characterized in that:
the block polymer is a film-forming linear ethylenic polymer,
the plasticizer being as described below.

Another subject matter of the invention is a cosmetic composition, in particular for making up or caring for keratinous substances, especially the skin or lips, comprising a cosmetically acceptable organic liquid medium, a block polymer and a plasticizer, characterized in that:
the block polymer is a film-forming linear ethylenic polymer,
the plasticizer is a compound having a solubility parameter $\delta_h$ ranging from 5.5 to 11 $(J/cm^3)^{1/2}$.

The block polymer is advantageously devoid of styrene.
More advantageously, the block polymer is non-elastomeric.

Preferably again, the block polymer comprises at least one first block and at least one second block having different glass transition temperatures (Tg), said first and second blocks being connected to one another via an intermediate block comprising at least one constituent monomer of the first block and at least one constituent monomer of the second block.

It is specified that, in that which precedes and in that which follows, the terms "first" and "second" blocks in no way condition the order of said blocks in the structure of the polymer.

The term "'at least' one block" is understood to mean one or more blocks.

Preferably, the polymer has a polydispersity index I of greater than 2.

Preferably again, the first and second blocks are incompatible with one another.

The composition according to the invention makes it possible to obtain a deposited layer, in particular a makeup deposited layer, on keratinous substances, in particular the skin or lips, having good gloss and transfer-free properties.

The composition according to the invention also makes it possible to obtain a deposited layer on keratinous substances, in particular on the skin or lips, which does not exhibit a feeling of dryness or tightness: the deposited layer thus obtained is therefore comfortable over time for the user.

Another subject matter of the invention is a process for making up keratinous substances, in particular the skin or lips, comprising the application to keratinous substances, in particular to the skin or lips, of a composition as defined above.

Another subject matter of the invention is the use of a composition as defined above for producing a deposited layer, in particular a makeup, on keratinous substances, in particular on the skin or lips, which is flexible and/or comfortable over time.

A further subject matter of the invention is the use, in a cosmetic composition comprising a cosmetically acceptable organic liquid medium,
of a film-forming linear ethylenic block polymer,
and of a plasticizer having a solubility parameter $\delta_h$ ranging from 5.5 to 11 $(J/cm^3)^{1/2}$, for producing a deposited layer, in particular a makeup, on keratinous substances, in particular on the skin or lips, which is flexible and/or comfortable over time.

The term "cosmetically acceptable organic liquid medium" is understood to mean a medium comprising at least one organic compound which is liquid at ambient temperature (25° C.) and atmospheric pressure ($10^5$ Pa) and which is compatible with keratinous substances, in particular the skin or lips, such as the oils or organic solvents commonly employed in cosmetic compositions.

The block polymer of the composition according to the invention is a film-forming linear block ethylenic polymer.

The term "'ethylenic' polymer" is understood to mean a polymer obtained by polymerization of monomers comprising an ethylenic unsaturation.

The term "'block' polymer" is understood to mean a polymer comprising at least 2 distinct blocks, preferably at least 3 distinct blocks.

The polymer is a polymer with a linear structure. In contrast, a polymer with a nonlinear structure is, for example, a polymer with a branched, star, grafted or other structure.

The term "'film-forming' polymer" is understood to mean a polymer capable of forming, by itself alone or in the presence of an additional agent which is able to form a film, a continuous film which adheres to a support, in particular to keratinous substances.

The term "blocks incompatible with one another" is understood to mean that the blend formed from the polymer corresponding to the first block and from the polymer corresponding to the second block is immiscible in the organic liquid, predominant by weight, of the organic liquid medium of the composition, at ambient temperature (25° C.) and atmospheric pressure ($10^5$ Pa), for a content of the blend of polymers of greater than or equal to 5% by weight, with respect to the total weight of the mixture (polymers and solvent), it being understood that:

i) said polymers are present in the blend in a content such that the respective ratio by weight ranges from 10/90 to 90/10, and that ii) each of the polymers corresponding to the first and second blocks has a weight-average or number-average molecular mass equal to that of the block polymer ±15%.

In the case where the organic liquid medium comprises a mixture of organic liquids and in the event of two or more organic liquids present in identical proportions by weight, said blend of polymers is immiscible in at least one of them.

Of course, in the case where the organic liquid medium comprises a single organic liquid, the latter is the predominant organic liquid.

Advantageously, the predominant organic liquid of the composition is the organic solvent for the polymerization of the block polymer or the predominant organic solvent of the mixture of organic solvents for the polymerization of the block polymer.

The intermediate block is a block comprising at least one constituent monomer of the first block and at least one constituent monomer of the second block of the polymer which makes it possible to "compatibilize" these blocks.

Preferably, the polymer used in the composition according to the invention does not comprise silicon atoms in its backbone. The term "backbone" is understood to mean the main chain of the polymer, in contrast to the pendent side chains.

Preferably, the polymer used in the composition according to the invention is not water-soluble, that is to say that the polymer is not soluble in water or in a mixture of water and of linear or branched lower monoalcohols having from 2 to 5 carbon atoms, such as ethanol, isopropanol or n-propanol, without modification of pH, at an active material content of at least 1% by weight, at ambient temperature (25° C.).

Preferably, the polymer used in the composition according to the invention is not an elastomer.

The term "non-elastomeric polymer" is understood to mean a polymer which, when it is subjected to a stress targeted at drawing it (for example by 30% relative to its initial length), does not return to a length substantially identical to its initial length when the stress ceases.

More specifically, the term "non-elastomeric polymer" denotes a polymer having an instantaneous recovery $R_i$<50% and a delayed recovery $R_{2h}$<70% after having undergone an elongation of 30%. Preferably, $R_i$ is <30% and $R_{2h}$<50%.

More specifically, the non-elastomeric nature of the polymer is determined according to the following protocol:

A polymer film is prepared by pouring a solution of the polymer into a Teflon-treated matrix and then drying for 7 days in surroundings controlled at 23±5° C. and 50±10% relative humidity.

A film with a thickness of approximately 100 μm is then obtained, from which rectangular test specimens with a width of 15 mm and a length of 80 mm are cut (for example with a hollow punch).

A tensile stress is applied to the sample using a device sold under the Zwick reference, under the same temperature and humidity conditions as for the drying.

The test specimens are drawn at a rate of 50 mm/min and the distance between the clamping jaws is 50 mm, which corresponds to the initial length ($I_0$) of the test specimen.

The instantaneous recovery $R_i$ is determined in the following way:

the test specimen is drawn by 30% ($\epsilon_{max}$), that is to say approximately 0.3 times its initial length ($I_0$), the stress is released by applying a return rate equal to the tensioning rate, i.e. 50 mm/min, and the residual elongation of the test specimen is measured as a percentage, after returning to zero stress ($\epsilon_i$).

The instantaneous recovery in % ($R_i$) is given by the formula below:

$$R_i = (\epsilon_{max} - \epsilon_i)/\epsilon_{max} \times 100$$

To determine the delayed recovery, the residual elongation of the test specimen is measured as percentage ($\epsilon_{2h}$).

The delayed recovery in % ($R_{2h}$) is given by the formula below:

$$R_{2h} = (\epsilon_{max} - \epsilon_{2h})/\epsilon_{max} \times 100$$

Purely by way of indication, a polymer used according to an embodiment of the invention has an instantaneous recovery $R_i$ of 10% and a delayed recovery $R_{2h}$ of 30%.

The polydispersity index I of the polymer is equal to the ratio of the weight-average mass Mw to the number-average mass Mn.

The weight-average molar masses (Mw) and the number-average molar masses (Mn) are determined by gel permeation liquid chromatography (solvent THF, calibration curve drawn up with linear polystyrene standards, refractometric detector).

The weight-average mass (Mw) of the polymer used in the composition according to the invention is preferably less than or equal to 300 000, it ranges, for example, from 35 000 to 200 000 and better still from 45 000 to 150 000.

The number-average mass (Mn) of the polymer used in the composition according to the invention is preferably less than or equal to 70 000, it ranges, for example, from 10 000 to 60 000 and better still from 12 000 to 50 000.

The polydispersity index of the polymer used in the composition according to the invention is greater than 2, for example is greater than 2 and less than or equal to 9, preferably greater than or equal to 2.5, for example ranging from 2.5 to 8, and better still greater than or equal to 2.8, in particular from 2.8 to 6.

Each block of the polymer used in the composition according to the invention results from one type of monomer or from several different types of monomers.

This means that each block can be composed of a homopolymer or of a copolymer; this copolymer constituting the block being able, in its turn, to be random or alternating.

Advantageously, the intermediate block comprising at least one constituent monomer of the first block and at least one constituent monomer of the second block of the polymer is a random polymer.

Preferably, the intermediate block results essentially from constituent monomers of the first block and of the second block.

The term "essentially" is understood to mean at least to 85%, preferably at least to 90%, better still to 95% and even better still to 100%.

Advantageously, the intermediate block has a glass transition temperature Tg between the glass-transition temperatures of the first and second blocks.

The glass transition temperatures indicated for the first and second blocks can be theoretical Tg values determined from the theoretical Tg values of the constituent monomers of each of the blocks, which can be found in a reference handbook, such as the Polymer Handbook, 3rd ed., 1989, John Wiley, according to the following relationship, referred to as the Fox law:

$$1/Tg = \sum_i (\omega_i/Tg_i),$$

$\omega_i$ being the mass fraction of the monomer i in the block under consideration and $Tg_i$ being the glass transition temperature of the homopolymer of the monomer i.

Unless otherwise indicated, the Tg values indicated for the first and second blocks in the present patent application are theoretical Tg values.

Advantageously, the first and second blocks of the polymer are such that the difference between the glass transition temperatures of the first and second blocks is generally greater than 10° C., preferably greater than 20° C. and better still greater than 30° C.

In particular, the first block can be chosen from:
a) a block having a Tg of greater than or equal to 40° C.,
b) a block having a Tg of less than or equal to 20° C.,
c) a block having a Tg of between 20 and 40° C.,
and the second block chosen from a category a), b) or c) different from the first block.

In the present invention, the expression: "of between . . . and . . . " is intended to denote a range of values, the limits of which mentioned are excluded, and "from . . . to . . . " and "ranging from . . . to . . . " is intended to denote a range of values, the limits of which are included.

a) Block Having a Tg of Greater than or Equal to 40° C.

The block having a Tg of greater than or equal to 40° C. for example has a Tg ranging from 40 to 150° C., preferably of greater than or equal to 50° C., for example ranging from 50° C. to 120° C., and better still of greater than or equal to 60° C., for example ranging from 60° C. to 120° C.

The block having a Tg of greater than or equal to 40° C. can be a homopolymer or a copolymer.

In the case where this block is a homopolymer, it results from a monomer, the homopolymer of which has a glass transition temperature of greater than or equal to 40° C.

In the case where the first block is a copolymer, it can result, in all or in part, from one or more monomers, the natures and the concentrations of which are chosen so that the Tg of the resulting copolymer is greater than or equal to 40° C. The copolymer can, for example, comprise:
monomers, the homopolymer of which has a Tg of greater than or equal to 40° C., for example a Tg ranging from 40 to 150° C., preferably of greater than or equal to 50° C., for example ranging from 50° C. to 120° C., and better still of greater than or equal to 60° C., for example ranging from 60° C. to 120° C., and
monomers, the homopolymer of which has a Tg of less than 40° C., chosen from monomers, the homopolymer of which has a Tg of between 20 and 40° C., and/or monomers, the homopolymer of which has a Tg of less than or equal to 20° C., for example a Tg ranging from −100 to 20° C., preferably of less than 15° C., in particular ranging from −80° C. to 15° C. and better still of less than 10° C., for example ranging from −50° C. to 0° C., as described later.

The monomers, the homopolymer of which has a glass transition temperature of greater than or equal to 40° C., are preferably chosen from the following monomers, also known as main monomers:

methacrylates of formula $CH_2=C(CH_3)-COOR_1$,
in which $R_1$ represents an unsubstituted linear or branched alkyl group comprising from 1 to 4 carbon atoms, such as a methyl, ethyl, propyl or isobutyl group, or $R_1$ represents a $C_4$ to $C_{12}$ cycloalkyl group, acrylates of formula $CH_2=CH-COOR_2$,
in which $R_2$ represents a $C_4$ to $C_{12}$ cycloalkyl group, such as an isobornyl group, or a tert-butyl group, (meth)acrylamides of formula:

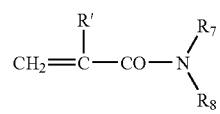

where $R_7$ and $R_8$, which are identical or different, each represent a hydrogen atom or a linear or branched $C_1$ to $C_{12}$ alkyl group, such as an n-butyl, t-butyl, isopropyl, isohexyl, isooctyl or isononyl group, or $R_7$ represents H and $R_8$ represents a 1,1-dimethyl-3-oxobutyl group, and R' denotes H or methyl; mention may be made, as examples of monomers, of N-butylacrylamide, N-t-butylacrylamide, N-isopropylacrylamide, N,N-dimethylacrylamide and N,N-dibutylacrylamide, and their mixtures.

Main monomers which are particularly preferred are methyl methacrylate, isobutyl (meth)acrylate, isobornyl (meth)acrylate and their mixtures.

b) Block Having a Tg of Less than or Equal to 20° C.

The block having a Tg of less than or equal to 20° C. for example has a Tg ranging from −100 to 20° C., preferably of less than or equal to 15° C., in particular ranging from −80° C. to 15° C. and better still of less than or equal to 10° C., for example ranging from −50° C. to 0° C.

The block having a Tg of less than or equal to 20° C. can be a homopolymer or a copolymer.

In the case where this block is a homopolymer, it results from monomers which are such that the homopolymers prepared from these monomers have glass transition temperatures of less than or equal to 20° C. This second block can be a homopolymer composed of a single type of monomer (the Tg of the corresponding homopolymer of which is less than or equal to 20° C.).

In the case where the block having a Tg of less than or equal to 20° C. is a copolymer, it can result, in all or in part, from one or more monomers, the natures and the concentrations of which are chosen so that the Tg of the resulting copolymer is less than or equal to 20° C.

It can, for example, comprise
one or more monomers, the corresponding homopolymer of which has a Tg of less than or equal to 20° C., for example a Tg ranging from −100° C. to 20° C., preferably of less than 15° C., in particular ranging from −80° C. to 15° C. and better still of less than 10° C., for example ranging from −50° C. to 0° C., and
one or more monomers, the corresponding homopolymer of which has a Tg of greater than 20° C., such as the monomers having a Tg of greater than or equal to 40° C., for example a Tg ranging from 40 to 150° C., preferably of greater than or equal to 50° C., for example ranging from 50° C. to 120° C., and better still of greater than or equal to 60° C., for example ranging from 60° C. to 120° C., and/or the monomers having a Tg of between 20 and 40° C., as described above.

Preferably, the block having a Tg of less than or equal to 20° C. is a homopolymer.

The monomers, the homopolymer of which has a Tg of less than or equal to 20° C., are preferably chosen from the following monomers, or main monomers:
acrylates of formula $CH_2=CHCOOR_3$,
$R_3$ representing an unsubstituted linear or branched $C_1$ to $C_{12}$ alkyl group, with the exception of the tert-butyl group, in which one or more heteroatoms chosen from O, N or S is (are) optionally inserted,
methacrylates of formula $CH_2=C(CH_3)-COOR_4$,
$R_4$ representing an unsubstituted linear or branched $C_6$ to $C_{12}$ alkyl group in which one or more heteroatoms chosen from O, N and S is (are) optionally inserted,
vinyl esters of formula $R_5-CO-O-CH=CH_2$,
where $R_5$ represents a linear or branched $C_4$ to $C_{12}$ alkyl group,
$C_4$ to $C_{12}$ alkyl vinyl ethers, such as methyl vinyl ether and ethyl vinyl ether,
N—($C_4$ to $C_{12}$ alkyl)acrylamides, such as N-octylacrylamide,
and their mixtures.

The main monomers which are particularly preferred for the block having a Tg of less than or equal to 20° C. are alkyl acrylates, the alkyl chain of which comprises from 1 to 10 carbon atoms, with the exception of the tert-butyl group, such as methyl acrylate, isobutyl acrylate, 2-ethylhexyl acrylate and their mixtures.

c) Block Having a Tg of Between 20 and 40° C.

The block which has a Tg of between 20 and 40° C. can be a homopolymer or a copolymer.

In the case where this block is a homopolymer, it results from a monomer (or main monomer), the homopolymer of which has a glass transition temperature of between 20 and 40° C.

Monomers, the homopolymer of which has a glass transition temperature of between 20 and 40° C., are preferably chosen from n-butyl methacrylate, cyclodecyl acrylate, neopentyl acrylate, isodecyl-acrylamide and their mixtures.

In the case where the block having a Tg of between 20 and 40° C. is a copolymer, it results, in all or in part, from one or more monomers (or main monomers), the natures and the concentrations of which are chosen so that the Tg of the resulting copolymer is between 20 and 40° C.

Advantageously, the block having a Tg of between 20 and 40° C. is a copolymer resulting, in all or in part:
from main monomers, the corresponding homopolymer of which has a Tg of greater than or equal to 40° C., for example a Tg ranging from 40° C. to 150° C., preferably of greater than or equal to 50° C., for example ranging from 50 to 120° C., and better still of greater than or equal to 60° C., for example ranging from 60° C. to 120° C., as described above, and
from main monomers, the corresponding homopolymer of which has a Tg of less than or equal to 20° C., for example a Tg ranging from −100 to 20° C., preferably of less than or equal to 15° C., in particular ranging from −80° C. to 15° C. and better still of less than or equal to 10° C., for example ranging from −50° C. to 0° C., as described above,
said monomers being chosen so that the Tg of the copolymer forming the first block is between 20 and 40° C.

Such main monomers are chosen, for example, from methyl methacrylate, isobornyl acrylate, isobornyl methacrylate, butyl acrylate, 2-ethylhexyl acrylate and their mixtures.

Preferably, the proportion of the second block having a Tg of less than or equal to 20° C. ranges from 10 to 85% by weight of the polymer, better still from 20 to 70% and even better still from 20 to 50%.

According to one embodiment, the block polymer used in the composition according to the invention is devoid of styrene. The term "polymer devoid of styrene" is understood to mean a polymer comprising less than 10% by weight, preferably less than 5% by weight, preferably less than 2% by weight, again preferably less than 1% by weight of, which indeed does not comprise, a styrene monomer, such as styrene or styrene derivatives, such as, for example, methylstyrene, chlorostyrene or chloromethylstyrene.

According to one embodiment, the block polymer of the composition according to the invention results from aliphatic ethylenic monomers. The term "aliphatic monomer" is understood to mean a monomer not comprising any aromatic group.

Each of the blocks can nevertheless comprise a minor proportion of at least one constituent monomer of the other block.

Thus, the first block can comprise at least one constituent monomer of the second block, and vice versa.

Each of the first and/or second blocks can comprise, in addition to the monomers indicated above, one or more other monomers, known as additional monomers, different from the main monomers mentioned above.

The natures and the amounts of this or these additional monomers are chosen so that the block in which they occur has the desired glass transition temperature.

This additional monomer is chosen, for example, from:
hydrophilic monomers, such as:
monomers with ethylenic unsaturation(s) comprising at least one carboxylic or sulfonic acid functional group, such as, for example:
acrylic acid, methacrylic acid, crotonic acid, maleic anhydride, itaconic acid, fumaric acid, maleic acid, acrylamidopropanesulfonic acid, vinylbenzoic acid, vinylphosphoric acid and the salts of these,
monomers with ethylenic unsaturation(s) comprising at least one tertiary amine functional group, such as 2-vinylpyridine, 4-vinylpyridine, dimethylaminoethyl methacrylate, diethylaminoethyl methacrylate, dimethylaminopropylmethacrylamide and the salts of these, methacrylates of formula $CH_2=C(CH_3)-COOR_6$, in which $R_6$ represents a linear or branched alkyl group comprising from 1 to 4 carbon atoms, such as a methyl, ethyl, propyl or isobutyl group, said alkyl group being substituted by one or more substituents chosen from hydroxyl groups (such as 2-hydroxypropyl methacrylate or 2-hydroxyethyl methacrylate) and halogen atoms (Cl, Br, I or F), such as trifluoroethyl methacrylate, methacrylates of formula $CH_2=C(CH_3)-COOR_9$, $R_9$ representing a linear or branched $C_6$ to $C_{12}$ alkyl group in which one or more heteroatoms chosen from O, N and S is (are) optionally inserted, said alkyl group being substituted by one or more substituents chosen from hydroxyl groups and halogen atoms (Cl, Br, I or F), acrylates of formula $CH_2=CHCOOR_{10}$, $R_{10}$ representing a linear or branched $C_1$ to $C_{12}$ alkyl group substituted by one or more substituents chosen from hydroxyl groups and halogen atoms (Cl, Br, I and F), such as 2-hydroxypropyl acrylate and 2-hydroxyethyl acrylate, or $R_{10}$ representing a $(C_1-C_{12})$alkyl-O-POE (polyoxyethylene) with repetition of the oxyethylene unit from 5 to 30 times, for example methoxy-POE, or $R_{10}$ representing a polyoxyethylene group comprising from 5 to 30 ethylene oxide units, b) monomers with ethylenic unsaturation comprising one or more silicon atoms, such as methacryloyloxypropyltrimethoxysilane or methacryloyloxypropyltris(trimethylsiloxy)silane, and their mixtures.

Additional monomers which are particularly preferred are acrylic acid, methacrylic acid, trifluoroethyl methacrylate and their mixtures.

This or these additional monomers generally represent(s) an amount of less than or equal to 30% by weight, for example from 1 to 30% by weight, preferably from 5 to 20% by weight and preferably again from 7 to 15% by weight, of the total weight of the first and/or second blocks.

According to a preferred embodiment, the polymer used in the composition according to the invention is a non-silicone polymer, that is to say a polymer devoid of silicon atoms.

Preferably, each of the first and second blocks comprises at least one monomer chosen from (meth)acrylic acid esters as defined above and optionally a monomer chosen from (meth)acrylic acid, and their mixtures.

Advantageously, each of the first and second blocks results, in all, from at least one monomer chosen from (meth)acrylic acid esters as defined above and optionally a monomer chosen from (meth)acrylic acid, and their mixtures.

The polymer used in the composition according to the invention can be obtained by radical solution polymerization according to the following preparation process:

a portion of the polymerization solvent is introduced into a suitable reactor and is heated until the temperature appropriate for the polymerization is reached (typically between 60 and 120° C.), once this temperature has been reached, the constituent monomers of the first block are introduced in the presence of a portion of the polymerization initiator and, after a time T corresponding to a maximum degree of conversion of 90%, the constituent monomers of the second block and the other portion of the initiator are introduced, the mixture is allowed to react for a time T' (ranging from 3 to 6 h), at the end of which the mixture is brought back to ambient temperature, the polymer is obtained in solution in the polymerization solvent.

The term "polymerization solvent" is understood to mean a solvent or a mixture of solvents. The polymerization solvent can be chosen in particular from ethyl acetate, butyl acetate, alcohols, such as isopropanol or ethanol, aliphatic alkanes, such as isododecane, and their mixtures. Preferably, the polymerization solvent is a mixture of butyl acetate and isopropanol or isododecane.

According to a first embodiment, the polymer used in the composition according to the invention comprises at least one (in particular one) first block having a Tg of greater than or equal to 40° C., as described above in a), and at least one (in particular one) second block having a Tg of less than or equal to 20° C., as described above in b).

Preferably, the first block having a Tg of greater than or equal to 40° C. is a copolymer resulting from monomers, the homopolymer of which has a glass transition temperature of greater than or equal to 40° C., such as the monomers described above.

Advantageously, the second block having a Tg of less than or equal to 20° C. is a homopolymer, in particular resulting from monomers as described above.

Preferably, the proportion of the block having a Tg of greater than or equal to 40° C. ranges from 20 to 90% by weight of the polymer, better still from 30 to 80% and even better still from 50 to 70%.

Preferably, the proportion of the block having a Tg of less than or equal to 20° C. ranges from 5 to 75% by weight of the polymer, preferably from 15 to 50% and better still from 25 to 45%.

Thus, according to a first alternative form, the polymer used in the composition according to the invention can comprise:

a first block with a Tg of greater than or equal to 40° C., for example having a Tg ranging from 70 to 110° C., which is a methyl methacrylate/acrylic acid copolymer, a second block with a Tg of less than or equal to 20° C., for example ranging from 0 to 20° C., which is a methyl acrylate homopolymer, and an intermediate block which is a methyl methacrylate/acrylic acid/methyl acrylate copolymer.

According to a second alternative form, the polymer used in the composition according to the invention can comprise:

a first block with a Tg of greater than or equal to 40° C., for example ranging from 70 to 100° C., which is a methyl methacrylate/acrylic acid/trifluoro-ethyl methacrylate copolymer, a second block with a Tg of less than or equal to 20° C., for example ranging from 0 to 20° C., which is a methyl acrylate homopolymer, and an intermediate block which is a methyl methacrylate/acrylic acid/methyl acrylate/trifluoroethyl methacrylate random copolymer.

According to a third alternative form, the polymer used in the composition according to the invention can comprise:

a first block with a Tg of greater than or equal to 40° C., for example ranging from 85 to 115° C., which is an isobornyl acrylate/isobutyl methacrylate copolymer, a second block with a Tg of less than or equal to 20° C., for example ranging from −85 to −55° C., which is a 2-ethylhexyl acrylate homopolymer, and an intermediate block which is an isobornyl acrylate/isobutyl methacrylate/2-ethylhexyl acrylate random copolymer.

According to a fourth alternative form, the polymer used in the composition according to the invention can comprise:

a first block with a Tg of greater than or equal to 40° C., for example ranging from 85 to 115° C., which is an isobornyl acrylate/methyl methacrylate copolymer, a second block with a Tg of less than or equal to 20° C., for example ranging from −85 to −55° C., which is a 2-ethylhexyl acrylate homopolymer, and an intermediate block which is an isobornyl acrylate/methyl methacrylate/2-ethylhexyl acrylate random copolymer.

According to a fifth alternative form, the polymer used in the composition according to the invention can comprise:

a first block with a Tg of greater than or equal to 40° C., for example ranging from 95 to 125° C., which is an isobornyl acrylate/isobornyl methacrylate copolymer, a second block with a Tg of less than or equal to 20° C., for example ranging from −85 to −55° C., which is a 2-ethylhexyl acrylate homopolymer, and an intermediate block which is an isobornyl acrylate/isobornyl methacrylate/2-ethylhexyl acrylate random copolymer.

According to a sixth alternative form, the polymer used in the composition according to the invention can comprise:

a first block with a Tg of greater than or equal to 40° C., for example ranging from 85 to 115° C., which is an isobornyl methacrylate/isobutyl methacrylate copolymer, a second block with a Tg of less than or equal to 20° C., for example ranging from −35 to −5° C., which is an isobutyl acrylate homopolymer, and an intermediate block which is an isobornyl methacrylate/isobutyl methacrylate/isobutyl acrylate random copolymer.

According to a seventh alternative form, the polymer used in the composition according to the invention can comprise:

a first block with a Tg of greater than or equal to 40° C., for example ranging from 95 to 125° C., which is an isobornyl acrylate/isobornyl methacrylate copolymer, a second block with a Tg of less than or equal to 20° C., for example ranging from −35 to −5° C., which is an isobutyl acrylate homopolymer, and an intermediate block which is an isobornyl methacrylate/isobornyl methacrylate/isobutyl acrylate random copolymer.

According to an eighth alternative form, the polymer used in the composition according to the invention can comprise:

a first block with a Tg of greater than or equal to 40° C., for example ranging from 60 to 90° C., which is an isobornyl acrylate/isobutyl methacrylate copolymer, a second block with a Tg of less than or equal to 20° C., for example ranging from −35 to −5° C., which is an isobutyl acrylate homopolymer, and an intermediate block which is an isobornyl acrylate/isobutyl methacrylate/isobutyl acrylate random copolymer.

According to a second embodiment, the polymer used in the composition according to the invention comprises at least one (in particular one) first block having a glass transition temperature (Tg) of between 20 and 40° C., in accordance with the blocks described in c), and at least one (in particular one) second block having a glass transition temperature of less than or equal to 20° C., as described above in b), or a glass transition temperature of greater than or equal to 40° C., as described in a) above.

Preferably, the proportion of the first block having a Tg of between 20 and 40° C. ranges from 10 to 85% by weight of the polymer, better still from 30 to 80% and even better still from 50 to 70%.

When the second block is a block having a Tg of greater than or equal to 40° C., it is preferably present in a proportion ranging from 10 to 85% by weight of the polymer, better still from 20 to 70% and even better still from 30 to 70%.

When the second block is a block having a Tg of less than or equal to 20° C., it is preferably present in a proportion ranging from 10 to 85% by weight of the polymer, better still from 20 to 70% and even better still from 20 to 50%.

Preferably, the first block having a Tg of between 20 and 40° C. is a copolymer resulting from monomers which are such that the corresponding homopolymer has a Tg of greater than or equal to 40° C. and from monomers which are such that the corresponding homopolymer has a Tg of less than or equal to 20° C.

Advantageously, the second block having a Tg of less than or equal to 20° C. or having a Tg of greater than or equal to 40° C. is a homopolymer.

Thus, according to a first alternative form of this second embodiment, the polymer used in the composition according to the invention can comprise:

a first block with a Tg of between 20 and 40° C., for example having a Tg from 25 to 39° C., which is a copolymer comprising at least one methyl acrylate monomer, at least one methyl methacrylate monomer and at least one acrylic acid monomer, a second block with a Tg of greater than or equal to 40° C., for example ranging from 85 to 125° C., which is a homopolymer composed of methyl methacrylate monomers, and an intermediate block comprising at least one methyl acrylate, methyl methacrylate monomer, and an intermediate block comprising methyl methacrylate, at least one acrylic acid monomer and at least one methyl acrylate monomer.

According to a second alternative form of this second embodiment, the polymer used in the composition according to the invention can comprise:

a first block with a Tg of between 20 and 40° C., for example having a Tg from 21 to 39° C., which is an isobornyl acrylate/isobutyl methacrylate/2-ethylhexyl acrylate copolymer, a second block with a Tg of less than or equal to 20° C., for example ranging from −65 to −35° C., which is a methyl methacrylate homopolymer, and an intermediate block which is an isobornyl acrylate/isobutyl methacrylate/2-ethylhexyl acrylate random copolymer.

According to a third alternative form of this second embodiment, the polymer used in the composition according to the invention can comprise:

a first block with a Tg of between 20 and 40° C., for example having a Tg from 21 to 39° C., which is an isobornyl acrylate/methyl acrylate/acrylic acid copolymer, a second block with a Tg of greater than or equal to 40° C., for example ranging from 85 to 115° C., which is an isobornyl acrylate homopolymer, and an intermediate block which is an isobornyl acrylate/methyl acrylate/acrylic acid random copolymer.

The block polymer described above can be present in the composition according to the invention in a content ranging from 0.1% to 90% by weight, with respect to the total weight of the composition, preferably ranging from 0.5% to 50% by weight and preferably ranging from 0.5% to 30% by weight.

The plasticizer present in the composition according to the invention can be a compound, the nature and the amount of which are such that the composition is capable of forming a film having a hardness of less than or equal to 35 seconds, the hardness of the film being measured using a Persoz pendulum according to Standard NF-T-30-016.

Consequently, according to one embodiment of the invention, the composition comprises a block polymer as described above and a plasticizer, the nature and the amount of which are such that the composition is capable of forming a film having a hardness of less than or equal to 35 seconds, the hardness of the film being measured using a Persoz pendulum according to Standard NF-T-30-016.

The hardness of the film was measured for a layer with a thickness of 300 µm (before drying) deposited on a glass sheet heated at 30° C. and after drying for 23 hours in the ambient atmosphere and then for 1 hour at 70% relative humidity for a composition with a solvent medium or at 50% relative humidity for a composition with an aqueous medium. The hardness of the film obtained is measured according to Standard ASTM D-43-66 or Standard NF-T 30-016 (December 1991) using a Persoz pendulum.

Advantageously, the composition according to the invention is capable of forming a film having a hardness of less than or equal to 35 seconds, in particular ranging from 8 to 35 seconds, preferably of less than or equal to 30 seconds, in particular ranging from 10 to 30 seconds, and preferentially of less than or equal to 25 seconds, in particular ranging from 12 to 25 seconds.

The plasticizer present in the composition according to the invention can be a compound having a solubility parameter $\delta_h$ ranging from 5.5 to 11 $(J/cm^3)^{1/2}$.

Consequently, according to one embodiment of the invention, the composition comprises a block polymer as described above and a plasticizer which is a compound having a solubility parameter $\delta_h$ ranging from 5.5 to 11 $(J/cm^3)^{1/2}$.

The plasticizer present in the composition according to the invention can be a compound having a solubility parameter $\delta_h$ ranging from 5.5 to 11 $(J/cm^3)^{1/2}$, preferably ranging from 5.5 to 11, preferentially ranging from 5.9 to 11, preferably ranging from 7 to 10.5, preferably ranging from 9 to 10, more preferentially ranging from 8 to 10 $(J/cm^3)^{1/2}$.

Preferably, the plasticizing compound has a solubility parameter $\delta_p$ ranging from 1.5 to 4.5 $(J/cm^3)^{1/2}$, preferably ranging from 1.5 to 4 $(J/cm^3)^{1/2}$, preferably ranging from 1.5 to 3.5 $(J/cm^3)^{1/2}$, preferably again ranging from 2 to 3 $(J/cm^3)^{1/2}$.

The plasticizer is preferably liquid at ambient temperature and atmospheric pressure.

The definition of the Hansen solubility parameters is well known to a person skilled in the art and is described in particular in the paper by C. M. Hansen, "The Three-Dimensional Solubility Parameters", J. Paint Technol., 39, 105 (1967). These parameters are also disclosed in the document JP-A-08-109121 of Kao and the document by D. W. Van Krevelen, "Properties of Polymers" (1990), p. 190.

According to this Hansen space:

$\delta_p$ characterizes the forces of Debye interactions between permanent dipoles; and $\delta_h$ characterizes the forces of specific interactions (hydrogen bond, acid/base or donor/acceptor type, and the like).

The $\delta_p$ and $\delta_h$ parameters are generally expressed in $(J/cm^3)^{1/2}$. They are determined at ambient temperature (25° C.) and in particular according to the calculation method indicated in the above Kao patent document.

In the composition according to the invention, use may be made of a mixture of compounds satisfying the above relationships. In this case, the solubility parameters of the mixture are determined from those of the compounds taken separately, according to the following relationships:

$$\delta_{pmix}=\Sigma_i x_i \cdot \delta_{pi} \text{ and } \delta_{hmix}=\Sigma_i x_i \cdot \delta_{hi}$$

where xi represents the volume fraction of the compound i in the mixture.

It is within the scope of a person skilled in the art to determine the amounts of each compound in order to obtain a mixture of compounds corresponding to the above relationships.

Preferably, the plasticizer has a molecular mass of less than or equal to 5000 g/mol, preferably of less than or equal to 2000 g/mol, preferentially of less than or equal to 1000 g/mol and more preferentially of less than or equal to 900 g/mol. The plasticizer advantageously has a molecular mass of greater than or equal to 100 g/mol.

Advantageously, the plasticizer used according to the invention is an ester.

According to a first embodiment of the composition according to the invention, the plasticizer can be chosen from esters of at least one carboxylic acid comprising 1 to 7 carbon atoms and of a polyol comprising at least 4 hydroxyl groups.

Consequently, the invention relates to a composition comprising a block polymer as described above and a plasticizer chosen from esters of at least one carboxylic acid comprising 1 to 7 carbon atoms and of a polyol comprising at least 4 hydroxyl groups, said ester having a molecular mass of less than 5000 g/mol.

The polyol according to the invention can be a cyclized or open-chain monosaccharide-polyhydroxy-aldehyde (aldose) or polyhydroxyketone (ketose). The polyol is preferably a cyclized monosaccharide in the hemiacetal form.

Mention may be made, among aldoses, of D-ribose, D-xylose, L-arabinose, D-glucose (or α-D-glucopyranose, when it is in the cyclic hemiacetal form), D-mannose and D-galactose.

Mention may be made, among ketoses, of D-xylulose and D-fructose (or β-D-fructofuranose, when it is in the cyclic hemiacetal form).

The polyol can be a mono- or polysaccharide comprising from 1 to 10 monosaccharide units, preferably from 1 to 4, preferably again one or two monosaccharide units. The polyol can be chosen from erythritol, xylitol, sorbitol, glucose, sucrose, lactose or maltose.

The polyol according to the invention is preferably a disaccharide. Mention may be made, among disaccharides, of sucrose (also known as α-D-gluco-pyranosyl-(1-2)-β-D-fructofuranose), of lactose (also known as β-D-galactopyranosyl-(1-4)-β-D-glucopyranose) and of maltose (also known as α-D-glucopyranosyl-(1-4)-β-D-glucopyranose), and preferably of sucrose.

The polyol can be a polysaccharide composed of several identical monosaccharide units or of at least two different monosaccharide units.

The ester according to the invention can be composed of a polyol esterified by at least two different monocarboxylic acids or by at least three different monocarboxylic acids.

The ester according to the invention can be a copolymer of two esters, in particular a copolymer i) of a sucrose substituted by benzoyl groups and ii) of a sucrose substituted by acetyl and/or isobutyryl groups.

The carboxylic acid is preferably a monocarboxylic acid comprising from 1 to 7 carbon atoms, preferably from 1 to 5 carbon atoms, for example chosen from acetic, n-propanoic, isopropanoic, n-butanoic, isobutanoic, tert-butanoic, n-pentanoic and benzoic acids.

The ester can be obtained from at least two different monocarboxylic acids. According to one embodiment, the acid is an unsubstituted linear or branched acid.

The acid is preferably chosen from acetic acid, isobutyric acid, benzoic acid and their mixtures, and more preferably.

According to a preferred embodiment, the ester is sucrose diacetate hexa(2-methylpropanoate), such as that sold under the name "Sustane SAIB Food Grade Kosher" by Eastman Chemical.

According to a second embodiment of the composition according to the invention, the plasticizer can be chosen from esters of an aliphatic or aromatic polycarboxylic acid and of an aliphatic or aromatic alcohol comprising from 1 to 10 carbon atoms.

Consequently, the invention relates to a composition comprising a block polymer as described above and a plasticizer chosen from esters of an aliphatic or aromatic polycarboxylic acid and of an aliphatic or aromatic alcohol comprising from 1 to 10 carbon atoms.

The aliphatic or aromatic alcohol comprises from 1 to 10 carbon atoms, preferably from 1 to 8, for example from 1 to 6. It can be chosen from $R_1OH$ alcohols, such that $R_1$ represents methyl, ethyl, propyl, isopropyl, butyl, hexyl, ethylhexyl, decyl, isodecyl, benzyl or benzyl substituted by an alkyl comprising 1 to 3 carbon atoms, and their mixtures.

The aliphatic or aromatic polycarboxylic acid preferably comprises from 3 to 12 carbon atoms, preferably from 3 to 10 carbon atoms, preferably from 3 to 8 carbon atoms, for example 6 or 8 carbon atoms.

The aliphatic or aromatic polycarboxylic acid is advantageously chosen from dicarboxylic acids and tricarboxylic acids.

Mention may be made, among aliphatic dicarboxylic acids, of those of formula $HOOC-(CH_2)_n-COOH$, in which n is an integer ranging from 1 to 10, preferably ranging from 2 to 8, for example equal to 2, 4, 6 or 8.

Preference is given to the dicarboxylic acids chosen from succinic acid, adipic acid and sebacic acid.

Mention may be made, among aromatic dicarboxylic acids, of phthalic acid.

Mention may be made, among tricarboxylic acids, of the triacids which correspond to the formula:

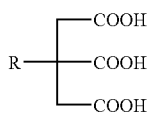

in which R represents an —H, —OH or —OCOR' group in which R' represents an alkyl group having from 1 to 6 carbon atoms. Preferably, R represents a —OCOCH$_3$ group.

The tricarboxylic acid is chosen in particular from acetylcitric acid, butyroylcitric acid or citric acid.

Use may be made, among tricarboxylic acid esters, of the esters derived from citric acid (or citrates), such as tributyl acetylcitrate, triethyl acetylcitrate, triethylhexyl acetylcitrate, trihexyl acetylcitrate, trihexyl butyroylcitrate, triisodecyl citrate, triisopropyl citrate, tributyl citrate and tri(2-ethylhexyl) citrate.

Mention may be made, among adipic acid esters, of dibutyl adipate and di(2-ethylhexyl) adipate.

Mention may be made, among sebacic acid esters, of dibutyl sebacate, di(2-ethylhexyl) sebacate, diethyl sebacate and diisopropyl sebacate.

Mention may be made, among succinic acid esters, of di(2-ethylhexyl) succinate and diethyl succinate.

Mention may be made, among phthalic acid esters, of butyl benzyl phthalate, dibutyl phthalate, diethylhexyl phthalate, diethyl phthalate and dimethyl phthalate.

The plasticizer preferably does not comprise any polar group with the exception of the ester group and in particular does not comprise any hydroxyl group. The "polar groups" are, for example, ionic or non-ionic polar groups chosen from —COOH, —OH, ethylene oxide, propylene oxide, —PO$_4$, —NHR or —NR$_1$R$_2$ with R$_1$ and R$_2$ representing a C$_1$ to C$_{20}$ alkyl or alkoxy radical which can be linear, branched or cyclic.

Advantageously, the block polymer and the plasticizer can be present in the composition in a content such that the ratio by weight of the block polymer to the plasticizer is between 0.5 and 100, preferably between 1 and 50, preferably between 1 and 10, preferably again between 1 and 5.

According to a particularly preferred embodiment, the organic liquid medium of the composition comprises at least one organic liquid which is the organic solvent or one of the organic solvents for the polymerization of the block polymer as described above. Advantageously, said organic solvent for the polymerization is the organic liquid predominant by weight in the organic liquid medium of the cosmetic composition.

The composition according to the invention can additionally comprise at least one volatile oil.

The term "oil" is understood to mean any nonaqueous medium which is liquid at ambient temperature (25° C.) and atmospheric pressure (760 mm of Hg) and which is compatible with an application to the skin, mucus membranes (lips) and/or superficial body growths (nails, eyelashes, eyebrows, hair).

The term "volatile oil" is understood to mean any nonaqueous medium capable of evaporating from the skin or lips in less than one hour and having in particular a vapor pressure, at ambient temperature and atmospheric pressure, ranging from $10^{-3}$ to 300 mm of Hg (0.13 Pa to 40 000 Pa).

According to the invention, use may be made of one or more volatile oils.

These oils can be hydrocarbon oils or silicone oils optionally comprising pendent alkyl or alkoxy groups or alkyl or alkoxy groups at the end of the silicone chain.

The term "hydrocarbon oil" is understood to mean an oil formed essentially, indeed even composed, of carbon and hydrogen atoms and optionally of oxygen or of nitrogen atoms and not comprising a silicon or fluorine atom. It can comprise alcohol, ester, ether, carboxylic acid, amine and/or amide groups.

Mention may be made, as volatile silicone oil which can be used in the invention, of linear or cyclic silicones having from 2 to 7 silicon atoms, these silicones optionally comprising alkyl or alkoxy groups having from 1 to 10 carbon atoms. Mention may in particular be made, as volatile silicone oil which can be used in the invention, of octamethylcyclotetrasiloxane, decamethylcyclopentasiloxane, dodecamethylcyclohexasiloxane, heptamethylhexyltrisiloxane, heptamethyloctyltrisiloxane, octamethyltrisiloxane, decamethyltetrasiloxane and their mixtures.

Preference is given in particular, as other volatile oil which can be used in the invention, to C$_8$-C$_{16}$ isoparaffins, such as isododecane, isodecane, isohexadecane and, for example, the oils sold under the trade names of Isopar or Permethyl, and in particular isododecane (Permethyl 99A).

The volatile oil can be present in the composition according to the invention in a content ranging from 0.1% to 90% by weight, with respect to the total weight of the composition, preferably ranging from 1% to 70% by weight and preferentially ranging from 5% to 50% by weight.

The composition according to the invention can comprise a nonvolatile oil.

The term "nonvolatile oil" is understood to mean an oil capable of remaining on the skin at ambient temperature (25° C.) and atmospheric pressure for at least one hour and having in particular a nonzero vapor pressure at ambient temperature (25° C.) and atmospheric pressure of less than 0.01 mm of Hg (1.33 Pa).

The nonvolatile oil can be chosen from nonvolatile silicone or hydrocarbon oils.

The term "hydrocarbon oil" is understood to mean an oil formed essentially, indeed even composed, of carbon and hydrogen atoms and optionally of oxygen or of nitrogen atoms and not comprising a silicon or fluorine atom. It can comprise alcohol, ester, ether, carboxylic acid, amine and/or amide groups.

The nonvolatile oil can be chosen from nonvolatile nonpolar oils, nonvolatile polar oils, and their mixtures.

The nonvolatile oil can be present in the composition according to the invention in a content ranging from 0.1% to 20% by weight, with respect to the total weight of the composition, preferably ranging from 1% to 15% by weight and preferentially ranging from 1% to 10% by weight.

Mention may be made, as nonvolatile oils which can be used in the invention, of:

nonvolatile hydrocarbon oils, such as liquid paraffin (or petrolatum), squalane, hydrogenated polyisobutylene (parleam oil), perhydrosqualene, mink oil, turtle oil, soybean oil, sweet almond oil, calophyllum oil, palm oil, grape seed oil, sesame oil, maize oil, arara oil, rapeseed oil, sunflower oil, cottonseed oil, apricot oil, castor oil, avocado oil, jojoba oil, olive oil or cereal germ oil; esters of lanolic acid, of oleic acid, of lauric acid, of stearic acid; fatty esters, in particular $C_{12}$-$C_{36}$ fatty esters, such as isopropyl myristate, isopropyl palmitate, butyl stearate, hexyl laurate, diisopropyl adipate, isononyl isononanoate, 2-ethylhexyl palmitate, 2-hexyldecyl laurate, 2-octyldecyl palmitate, 2-octyldodecyl myristate, 2-octyldodecyl lactate, di(2-ethylhexyl) succinate, diisostearyl malate, glyceryl triisostearate or diglyceryl triisostearate; higher fatty acids, in particular $C_{14}$-$C_{22}$ higher fatty acids, such as myristic acid, palmitic acid, stearic acid, behenic acid, oleic acid, linoleic acid, linolenic acid or isostearic acid; higher fatty alcohols, in particular $C_{16}$-$C_{22}$ higher fatty alcohols, such as cetanol, oleyl alcohol, linoleyl alcohol, linolenyl alcohol, isostearyl alcohol or octyldodecanol; and their mixtures;

nonvolatile silicone oils, such as nonvolatile polydimethylsiloxanes (PDMSs); polydimethylsiloxanes comprising pendent alkyl, alkoxy or phenyl groups or alkyl, alkoxy or phenyl groups at the end of the silicone chain, which groups have from 2 to 24 carbon atoms; phenylated silicones, such as phenyl trimethicones, phenyl dimethicones, phenyl(trimethylsiloxy)diphenylsiloxanes, diphenyl dimethicones or diphenyl(methyldiphenyl)trisiloxanes; polysiloxanes modified by fatty acids (in particular $C_8$-$C_{20}$ fatty acids), fatty alcohols (in particular $C_8$-$C_{20}$ fatty alcohols) or polyoxyalkylenes (in particular polyoxyethylene and/or polyoxypropylene); aminated silicones; silicones comprising hydroxyl groups; fluorosilicones comprising a pendent fluorinated group or a fluorinated group at the end of the silicone chain having from 1 to 12 carbon atoms, all or a portion of the hydrogens of which are substituted by fluorine atoms; and their mixtures.

Advantageously, the nonvolatile hydrocarbon oil is chosen from hydrocarbons, in particular alkanes, such as hydrogenated polyisobutene.

The composition can comprise, in addition to the block polymer described above according to the invention, an additional polymer, such as a film-forming polymer. According to the present invention, the term "film-forming polymer" is understood to mean a polymer capable of forming, by itself alone or in the presence of an additional agent which is able to form a film, a continuous film which adheres to a support, in particular to keratinous substances.

Mention may be made, among film-forming polymers which can be used in the composition of the present invention, of synthetic polymers of radical type or of polycondensate type, polymers of natural origin and their blends. Mention may in particular be made, as film-forming polymers, of acrylic polymers, polyurethanes, polyesters, polyamides, polyureas or cellulose polymers, such as nitrocellulose.

The composition according to the invention can also comprise at least one fatty substance which is solid at ambient temperature chosen in particular from waxes, pasty fatty substances, gums and their mixtures. These fatty substances can be of animal, vegetable, mineral or synthetic origin.

The term "wax" within the meaning of the present invention is understood to mean a lipophilic compound, solid at ambient temperature (25° C.), with a reversible solid/liquid change of state, having a melting point of greater than or equal to 30° C. which can range up to 120° C.

The melting point of the wax can be measured using a differential scanning calorimeter (DSC), for example the calorimeter sold under the name DSC 30 by Metler.

The waxes can be hydrocarbon, fluorinated and/or silicone waxes and can be of vegetable, mineral, animal and/or synthetic origin. In particular, the waxes exhibit a melting point of greater than 25° C. and better still of greater than 45° C.

Mention may be made, as wax which can be used in the composition of the invention, of beeswax, carnauba wax, candelilla wax, paraffin wax, microcrystalline waxes, ceresin or ozokerite; synthetic waxes, such as polyethylene wax or Fischer-Tropsch waxes; or silicone waxes, such as alkyl or alkoxy dimethicones having from 16 to 45 carbon atoms.

The gums are generally polydimethylsiloxanes (PDMSs) of high molecular weight or cellulose gums or polysaccharides and the pasty substances are generally hydrocarbon compounds, such as lanolins and their derivatives or alternatively PDMSs.

The natures and the amounts of the solid substances depend on the mechanical properties and textures desired. By way of indication, the composition can comprise from 0.1 to 50% by weight of waxes, with respect to the total weight of the composition, and better still from 1 to 30% by weight.

The composition according to the invention can additionally comprise one or more coloring materials chosen from water-soluble dyes and pulverulent coloring materials, such as pigments, pearlescent agents and glitter well known to a person skilled in the art. The coloring materials can be present in the composition in a content ranging from 0.01% to 50% by weight, with respect to the weight of the composition, preferably from 0.01% to 30% by weight.

The term "pigments" should be understood as meaning white or colored and inorganic or organic particles of any shape which are insoluble in the physiological medium and which are intended to color the composition.

The term "pearlescent agents" should be understood as meaning iridescent particles of any shape produced in particular by certain molluscs in their shells or else synthesized.

The pigments can be white or colored and inorganic or organic. Mention may be made, among inorganic pigments, of titanium dioxide, optionally surface-treated, zirconium or cerium oxides, and also zinc, iron (black, yellow or red) or chromium oxides, manganese violet, ultramarine blue, chromium hydrate and ferric blue, or metal powders, such as aluminium powder or copper powder.

Mention may be made, among organic pigments, of carbon black, pigments of D & C type, and lakes, based on cochineal carmine, of barium, strontium, calcium or aluminum.

Mention may also be made of pigments with an effect, such as particles comprising an organic or inorganic and natural or synthetic substrate, for example glass, acrylic resins, polyester, polyurethane, poly(ethylene terephthalate), ceramics or aluminas, said substrate being covered or not being covered with metal substances, such as aluminum, gold, silver, platinum, copper or bronze, or with metal oxides, such as titanium dioxide, iron oxide or chromium oxide, and their mixtures.

The pearlescent pigments can be chosen from white pearlescent pigments, such as mica covered with titanium oxide or with bismuth oxychloride, colored pearlescent pigments, such as titanium oxide-coated mica covered with iron oxide, titanium oxide-coated mica covered with in particular ferric blue or chromium oxide, or titanium oxide-coated mica covered with an organic pigment of the abovementioned type, and pearlescent pigments based on bismuth oxychloride. Use may also be made of interferential pigments, in particular liquid crystal or multilayer pigments.

The water-soluble dyes are, for example, beetroot juice or methylene blue.

The composition according to the invention can additionally comprise one or more fillers, in particular in a content ranging from 0.01% to 50% by weight, with respect to the total weight of the composition, preferably ranging from 0.01% to 30% by weight. The term "fillers" should be understood as meaning colorless or white and inorganic or synthetic particles of any shape which are insoluble in the medium of the composition, whatever the temperature at which the composition is manufactured. These fillers are used in particular to modify the rheology or the texture of the composition.

The fillers can be inorganic or organic fillers of any shape, platelet, spherical or oblong, whatever the crystallographic form (for example, leaf, cubic, hexagonal, orthorhombic, and the like). Mention may be made of talc, mica, silica, kaolin, polyamide (Nylon®) powders (Orgasol® from Atochem), poly-β-alanine powders, polyethylene powders, powders formed of tetrafluoroethylene polymers (Teflon®), lauroyllysine, starch, boron nitride, polymeric hollow microspheres, such as those of polyvinylidene chloride/acrylonitrile, for example Expancel® (Nobel Industry) or of acrylic acid copolymers (Polytrap® from Dow Corning), silicone resin microbeads (Tospearls® from Toshiba, for example), polyorganosiloxane elastomer particles, precipitated calcium carbonate, magnesium carbonate, basic magnesium carbonate, hydroxyapatite, hollow silica microspheres (Silica Beads® from Maprecos), glass or ceramic microcapsules, or metal soaps derived from organic carboxylic acids having from 8 to 22 carbon atoms, preferably from 12 to 18 carbon atoms, for example zinc stearate, magnesium stearate, lithium stearate, zinc laurate or magnesium myristate.

The composition according to the invention can also comprise ingredients commonly used in cosmetics, such as vitamins, thickeners, trace elements, softeners, sequestering agents, fragrances, basifying or acidifying agents, preservatives, sunscreen agents, surfactants, antioxidants, agents for combatting hair loss, antidandruff agents, propellants or their mixtures.

Of course, a person skilled in the art will take care to choose this or these optional additional compounds and/or their amounts so that the advantageous properties of the corresponding composition according to the invention are not, or not substantially, detrimentally affected by the envisaged addition.

The composition according to the invention can be provided in particular in the form of a suspension, dispersion, solution, gel, emulsion, in particular oil-in-water (O/W) or water-in-oil (W/O) or multiple (W/O/W or polyol/O/W or O/W/O) emulsion, cream, foam, dispersion of vesicles, in particular of ionic or nonionic lipids, two-phase or multiphase lotion, spray, powder or paste, in particular soft paste (in particular paste having a dynamic viscosity at 25° C. of the order of 0.1 to 40 Pa-s under a shear rate of 200 $s^{-1}$, after measuring for 10 minutes in cone/plate geometry). The composition can be anhydrous; for example, it can be an anhydrous stick or paste. The composition can be a leave-in composition.

A person skilled in the art can choose the appropriate dosage form and its method of preparation on the basis of his general knowledge, taking into account, on the one hand, the nature of the constituents used, in particular their solubility in the support, and, on the other hand, the application envisaged for the composition.

According to another aspect, the invention also relates to a cosmetic combination comprising:

i) a container delimiting at least one compartment, said container being closed by a closing element; and ii) a composition positioned inside said compartment, the composition being in accordance with the invention.

The container can have any appropriate form. It can in particular be in the form of a bottle, a tube, a pot, a box, a tin, a bag or a case.

The closing element can be in the form of a removable stopper, of a lid, of a seal, of a tear-off strip or of a capsule, in particular of the type comprising a body fixed to the container and a cap articulated over the body. It can also be in the form of an element providing the selective closure of the container, in particular a pump, a valve or a flap.

The container can be used in combination with an applicator, in particular in the form of a brush comprising an arrangement of hairs held by a twisted wire. Such a twisted brush is disclosed in particular in U.S. Pat. No. 4,887,622. It can also be in the form of a comb comprising a plurality of application elements, obtained in particular from moulding. Such combs are disclosed, for example, in Patent FR 2 796 529. The applicator can be in the form of a fine brush, such as disclosed, for example, in Patent FR 2 722 380. The applicator can be in the form of a pad of foam or elastomer, of a felt-tipped pen or of a spatula. The applicator can be free (powder puff or sponge) or integrally attached to a shaft carried by the closing element, such as disclosed, for example, in U.S. Pat. No. 5,492,426. The applicator can be integrally attached to the container, such as described, for example, in Patent FR 2 761 959.

The product may be contained directly in the container or indirectly. By way of example, the product can be positioned on an impregnated support, particularly in the form of a wipe or of a wad, and can be positioned (singly or severally) in a tin or in a bag. Such a support incorporating the product is disclosed, for example, in Application WO 01/03538.

The closing element can be coupled to the container by screwing. Alternatively, the coupling between the closing element and the container is carried out other than by screwing, in particular via a bayonet mechanism, by snapping, clamping, welding or adhesive bonding, or by magnetic attraction. The term "snapping" is understood to mean in particular any system involving the crossing of a row or strip of material by elastic deformation of a portion, in particular of the closing element, and then by elastically returning said portion to the unstressed position after the row or strip has been crossed.

The container can be at least partially made of thermoplastic material. Mention may be made, as examples of thermoplastic materials, of polypropylene or polyethylene.

Alternatively, the container is made of nonthermoplastic material, in particular of glass or of metal (or alloy).

The container can have rigid walls or deformable walls, in particular in the form of a tube or of a tube bottle.

The container can comprise means intended to bring about or facilitate the distribution of the composition. By way of example, the container can have deformable walls, so as to bring about the departure of the composition in response to excess pressurization inside the container, which excess pressurization is brought about by the elastic (or nonelastic) crushing of the walls of the container. Alternatively, in particular when the product is in the form of a stick, the latter can be driven by a piston mechanism. Still in the case of a stick, in particular of a makeup product (lipstick, foundation, and the like), the container can comprise a mechanism, in particular a rack-and-pinion mechanism or a mechanism with a screw rod or a mechanism with a helical groove, capable of moving a stick in the direction of said opening. Such a mechanism is disclosed, for example, in Patent FR 2 806 273 or in Patent FR 2 775 566. Such a mechanism for a liquid product is disclosed in Patent FR 2 727 609.

The container can be composed of a case with a bottom delimiting at least one receptacle comprising the composition and a lid, in particular articulated over the bottom, capable of at least partially covering said bottom. Such a case is disclosed, for example, in Application WO 03/018423 or in Patent FR 2 791 042.

The container can be equipped with a drainer positioned in the vicinity of the opening of the container. Such a drainer makes it possible to wipe the applicator and optionally the rod to which it may be integrally attached. Such a drainer is disclosed, for example, in Patent FR 2 792 618.

The composition can be at atmospheric pressure inside the container (at ambient temperature) or pressurized, in particular using a propellant gas (aerosol). In the latter case, the container is equipped with a valve (of the type of those used for aerosols).

The contents of the abovementioned patents or patent applications are incorporated by reference in the present patent application.

The invention is illustrated in more detail by the examples described below.

EXAMPLE 1

Preparation of a poly(isobornyl acrylate/isobornyl methacrylate/2-ethylhexyl acrylate) polymer 100 g of isododecane are introduced into a 1 liter reactor and then the temperature is increased so as to change from ambient temperature (25° C.) to 90° C. over 1 hour.

105 g of isobornyl acrylate, 105 g of isobornyl methacrylate, 110 g of isododecane and 1.8 g of 2,5-bis(2-ethylhexanoylperoxy)-2,5-dimethylhexane (Trigonox® 141 from Akzo Nobel) are subsequently added at 90° C. over 1 hour.

The mixture is maintained at 90° C. for 1 h 30.

90 g of 2-ethylhexyl acrylate, 90 g of isododecane and 1.2 g of 2,5-bis(2-ethylhexanoylperoxy)-2,5-dimethylhexane are subsequently introduced into the preceding mixture, still at 90° C., over 30 minutes.

The mixture is maintained at 90° C. for 3 hours and then the combined product is cooled.

A solution comprising 50% of polymer active material in isododecane is obtained.

A polymer comprising a first poly(isobornyl acrylate/isobornyl methacrylate) block having a Tg of 110° C., a second poly(2-ethylhexyl acrylate) block having a Tg of −70° C. and an intermediate block which is an isobornyl acrylate/isobornyl methacrylate/2-ethylhexyl acrylate random polymer is obtained.

This polymer exhibits a weight-average mass of 103 900 and a number-average mass of 21 300, i.e. a polydispersity index I of 4.89.

EXAMPLE 2

A lipstick was prepared having the following composition:

| | |
|---|---|
| Block polymer of Example 1 at 50% by weight in isododecane | 50 g |
| Hydrophobically-treated pyrogenic silica (Aerosil R 972 from Degussa) | 5 g |
| Sucrose acetate isobutyrate (Eastman SAIB from Eastman Chemical) | 5 g |
| Hydrogenated polyisobutylene (parleam oil) | 2.1 g |
| Octyldodecanol | 0.9 g |
| Phenylated silicone oil (Dow Corning 556 C) | 2.1 g |
| Polyvinylpyrrolidone/eicosene copolymer (Antaron V220 from ISP) | 1.2 g |
| Pigments | 3 g |
| Isododecane | q.s. for 100 g |

The octyldodecanol, the silicone oil, the parleam oil, the sucrose acetate isobutyrate and the polyvinylpyrrolidone/eicosene copolymer are mixed while heating at approximately 60° C. A ground pigment mixture of the pigments is produced with this mixture by carrying out 3 passes of the mixture through the triple roll mill.

The ground pigment mixture, the isododecane and the block polymer are subsequently mixed at ambient temperature and then the silica is introduced at the end. The formulation is subsequently introduced into a leaktight boiling vessel.

The lipstick forms a film having a hardness of 20 seconds, measured with a Persoz pendulum according to the protocol described above.

This lipstick thus makes it possible to obtain a flexible makeup which is comfortable to wear over time and which exhibits good absence of transfer.

EXAMPLE 3

A lipstick not comprising plasticizer and thus not forming part of the invention was prepared with the following composition:

| | |
|---|---|
| Block polymer of Example 1 at 50% by weight in isododecane | 50 g |
| Hydrophobically-treated pyrogenic silica (Aerosil R 972 from Degussa) | 5 g |
| Hydrogenated polyisobutylene (parleam oil) | 2.1 g |
| Octyldodecanol | 0.9 g |
| Phenylated silicone oil (Dow Corning 556 C) | 2.1 g |
| Polyvinylpyrrolidone/eicosene copolymer (Antaron V220 from ISP) | 1.2 g |
| Pigments | 3 g |
| Isododecane | q.s. for 100 g |

This lipstick forms a film having a hardness of 42 seconds. It thus forms a less flexible makeup than that obtained with the lipstick of Example 2 according to the invention.

The invention claimed is:

1. A cosmetic composition comprising, in a cosmetically acceptable organic liquid medium, at least one block polymer and at least one plasticizer, wherein:
    the at least one block polymer has a polydispersity index I of greater than 2 and is a film-forming linear ethylenic polymer devoid of styrene;
    the at least one plasticizer is a compound, the nature and the amount of which allow the cosmetic composition to form a film having a hardness of less than or equal to 35 seconds, the hardness of the film being measured using a Persoz pendulum according to the December 1991 version of Standard NF-T-30-016; and
    the at least one block polymer comprises at least one first block and at least one second block having different glass transition temperatures (Tg), wherein the at least one first block and the at least one second block are connected to one another via an intermediate block comprising at least one constituent monomer of the at least one first block and at least one constituent monomer of the at least one second block, and further wherein said intermediate block is a random copolymer block.

2. The cosmetic composition according to claim 1, wherein the film has a hardness of less than 30 seconds.

3. The cosmetic composition according to claim 1, wherein the film has a hardness ranging from 8 to 35 seconds.

4. The cosmetic composition according to claim 1, wherein the film has a hardness ranging from 12 to 25 seconds.

5. The cosmetic composition according to claim 1, wherein the at least one plasticizer is a compound having a solubility parameter $\delta_h$ ranging from 5.5 to 11 $(J/cm^3)^{1/2}$.

6. The cosmetic composition according to claim 1, wherein the at least one block polymer is non-elastomeric.

7. The cosmetic composition according to claim 1, wherein the at least one first block and the at least one second block are incompatible with one another.

8. The cosmetic composition according to claim 1, wherein the at least one first block of the block polymer is chosen from:
    a) a block having a Tg of greater than or equal to 40° C.,
    b) a block having a Tg of less than or equal to 20° C.,
    c) a block having a Tg of between 20 and 40° C., and
    the at least one second block is chosen from a category a), b) and c) different from the at least one first block.

9. The cosmetic composition according to claim 1, wherein the at least one block polymer comprises at least one first block having a glass transition temperature (Tg) of greater than or equal to 40° C. and at least one second block having a glass transition temperature of less than or equal to 20° C.

10. The cosmetic composition according to claim 9, wherein the at least one first block is present in an amount ranging from 20 to 90% by weight relative to the total weight of the polymer.

11. The cosmetic composition according to claim 10, wherein the at least one first block is present in an amount ranging from 50 to 70% by weight relative to the total weight of the polymer.

12. The cosmetic composition according to claim 8, wherein the at least one second block having a Tg of less than or equal to 20° C. is present in an amount ranging from 5 to 75% by weight relative to the total weight of the polymer.

13. The cosmetic composition according to claim 12, wherein at least one second block having a Tg of less than or equal to 20° C. is present in an amount ranging from 25 to 45% by weight relative to the total weight of the polymer.

14. The cosmetic composition according to claim 1, wherein the at least one block polymer comprises at least one first block having a glass transition temperature (Tg) of between 20 and 40° C. and at least one second block having a glass transition temperature of less than or equal to 20° C. or a glass transition temperature of greater than or equal to 40° C.

15. The cosmetic composition according to claim 14, wherein the at least one first block having a Tg of between 20 and 40° C. is present in an amount ranging from 10 to 85% by weight relative to the total weight of the polymer.

16. The cosmetic composition according to claim 15, wherein the at least one first block having a Tg of between 20 and 40° C. is present in an amount ranging from 50 to 70% by weight relative to the total weight of the polymer.

17. The cosmetic composition according to claim 14, wherein the at least one second block has a Tg of greater than or equal to 40° C.

18. The cosmetic composition according to claim 14, wherein the at least one second block having a Tg of greater than or equal to 40° C. is present in an amount ranging from 10 to 85% by weight relative to the total weight of the polymer.

19. The cosmetic composition according to claim 18, wherein the at least one second block having a Tg of greater than or equal to 40° C. is present in an amount ranging from 30 to 70% by weight relative to the total weight of the polymer.

20. The cosmetic composition according to claim 14, wherein the at least one second block has a Tg of less than or equal to 20° C.

21. The cosmetic composition according to claim 8, wherein the at least one block having a glass transition temperature of less than or equal to 20° C. is present in an amount ranging from 20 to 90% by weight relative to the total weight of the polymer.

22. The cosmetic composition according to claim 8, wherein the at least one block having a glass transition temperature of less than or equal to 20° C. is present in an amount ranging from 50 to 70% by weight relative to the total weight of the polymer.

23. The cosmetic composition according to claim 8, wherein the block having a Tg of greater than or equal to 40° C. results, in all or in part, from at least one monomer, the homopolymer of which has a glass transition temperature of greater than or equal to 40° C.

24. The cosmetic composition according to claim 23, wherein the block having a Tg of greater than or equal to 40°

C. results, in all or in part, from at least one monomer, the homopolymer of which has a glass transition temperature ranging from 60 to 120° C.

25. The cosmetic composition according to claim 24, wherein the block having a Tg of greater than or equal to 40° C. is a copolymer resulting from the at least one monomer, the homopolymer of which has a glass transition temperature of greater than or equal to 40° C.

26. The cosmetic composition according to claim 23, wherein the at least one monomer, the homopolymer of which has a glass transition temperature of greater than or equal to 40° C., is chosen from the following monomers:
methacrylates of formula $CH_2=C(CH_3)—COOR_1$,
in which $R_1$ is chosen from an unsubstituted linear or branched $C_1$ to $C_4$ alkyl group and a $C_4$ to $C_{12}$ cycloalkyl group;
acrylates of formula $CH_2=CH—COOR_2$,
in which $R_2$ is chosen from a $C_4$ to $C_{12}$ cycloalkyl group and a tert-butyl group;
(meth)acrylamides of formula:

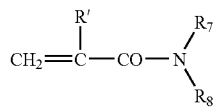

where $R_7$ and $R_8$, which are identical or different, each are chosen from a hydrogen atom and a linear or branched $C_1$ to $C_{12}$ alkyl group, or $R_7$ is hydrogen and $R_8$ is a 1,1-dimethyl-3-oxobutyl group, and R' is chosen from hydrogen and methyl;
and their mixtures.

27. The cosmetic composition according to claim 21, wherein the at least one monomer, the homopolymer of which has a glass transition temperature of greater than or equal to 40° C., is chosen from methyl methacrylate, isobutyl methacrylate, isobornyl (meth)acrylate and their mixtures.

28. The cosmetic composition according to claim 8, wherein the block having a Tg of greater than or equal to 40° C. is a homopolymer.

29. The cosmetic composition according to claim 8, wherein the block having a Tg of less than or equal to 20° C. results, in all or in part, from at least one monomer, the homopolymer of which has a glass transition temperature of less than or equal to 20° C.

30. The cosmetic composition according to claim 8, wherein the block having a Tg of less than or equal to 20° C. results, in all or in part, from at least one monomer, the homopolymer of which has a glass transition temperature ranging from −50 to 0° C.

31. The cosmetic composition according to claim 30, wherein the at least one monomer, the homopolymer of which has a glass transition temperature of less than or equal to 20° C., is chosen from the following monomers:
acrylates of formula $CH_2=CHCOOR_3$,
$R_3$ is an unsubstituted linear or branched $C_1$ to $C_{12}$ alkyl group, with the exception of the tert-butyl group, in which one or more heteroatoms chosen from O, N and S are optionally inserted;
methacrylates of formula $CH_2=C(CH_3)—COOR_4$,
$R_4$ is an unsubstituted linear or branched $C_6$ to $C_{12}$ alkyl group in which one or more heteroatoms chosen from O, N and S are optionally inserted;
vinyl esters of formula $R_5—CO—O—CH=CH_2$,
where $R_5$ is a linear or branched $C_4$ to $C_{12}$ alkyl group;
$C_4$ to $C_{12}$ alkyl vinyl ethers;
N—($C_4$ to $C_{12}$ alkyl)acrylamides;
and their mixtures.

32. The cosmetic composition according to claim 29, wherein the at least one monomer, the homopolymer of which has a glass transition temperature of less than or equal to 20° C., is chosen from $C_1$ to $C_{10}$ alkyl acrylates, with the exception of a tert-butyl group.

33. The cosmetic composition according to claim 15, wherein the block having a glass transition temperature of less than or equal to 20° C. is a homopolymer.

34. The cosmetic composition according to claim 8, wherein the block having a Tg of between 20 and 40° C. results, in all or in part, from at least one monomer, the homopolymer of which has a glass transition temperature of between 20 and 40° C.

35. The cosmetic composition according to claim 8, wherein the block having a Tg of between 20 and 40° C. is a homopolymer of at least one monomer chosen from n-butyl methacrylate, cyclodecyl acrylate, neopentyl acrylate and isodecylacrylamide.

36. The cosmetic composition according to claim 8, wherein the block having a Tg of between 20 and 40° C. is a copolymer resulting, in all or in part, from:
at least one monomer, the homopolymer of which has a Tg of greater than or equal to 40° C.; and
at least one monomer, the homopolymer of which has a Tg of less than or equal to 20° C.

37. The cosmetic composition according to claim 36, wherein the homopolymer of which has a Tg of greater than or equal to 40° C., ranges from 60 to 120° C. and the homopolymer of which has a Tg of less than or equal to 20° C., ranges from −50 to 0° C.

38. The cosmetic composition according to claim 8, wherein the block having a Tg of between 20 and 40° C. results, in all or in part, from at least one monomer chosen from methyl methacrylate, isobornyl (meth)acrylate, trifluoroethyl methacrylate, butyl acrylate, 2-ethylhexyl acrylate and their mixtures.

39. The cosmetic composition according to claim 8, wherein the at least one first block and/or the at least one second block comprises at least one additional monomer.

40. The cosmetic composition according to claim 39, wherein the at least one additional monomer is chosen from hydrophilic monomers, monomers with ethylenic unsaturation comprising at least one silicon atom, and their mixtures.

41. The cosmetic composition according to claim 39, wherein the at least one additional monomer is chosen from:
monomers with ethylenic unsaturation(s) comprising at least one carboxylic or sulfonic acid functional group;
methacrylates of formula $CH_2=C(CH_3)—COOR_6$;
in which $R_6$ is a linear or branched $C_1$ to $C_4$ alkyl group, said alkyl group being substituted by at least one substituent chosen from a hydroxyl group and halogen atoms;
methacrylates of formula $CH_2=C(CH_3)—COOR_9$,
$R_9$ is a linear or branched $C_6$ to $C_{12}$ alkyl group into which one or more heteroatoms chosen from O, N and S are optionally inserted, the alkyl group being substituted by at least one substituent chosen from a hydroxyl group and halogen atoms;
acrylates of formula $CH_2=CHCOOR_{10}$,
$R_{10}$ is a linear or branched $C_1$ to $C_{12}$ alkyl group substituted by at least one substituent chosen from a hydroxyl group and halogen atoms, or $R_{10}$ is a $(C_1$-$C_{12})$alkyl-O—POE (polyoxyethylene) with repetition of the oxyethylene unit from 5 to 30 times, or $R_{10}$ is a polyoxyethylene group comprising from 5 to 30 ethylene oxide units;
monomers with ethylenic unsaturation(s) comprising at least one tertiary amine functional group;
and their mixtures.

42. The cosmetic composition according to claim 39, wherein the at least one additional monomer is chosen from acrylic acid, methacrylic acid, trifluoroethyl methacrylate and their mixtures.

43. The cosmetic composition according to claim 39, wherein the at least one additional monomer is present in an amount ranging from 1 to 30% by weight of the total weight of the at least one first block and/or the at least one second block.

44. The cosmetic composition according to claim 8, wherein each of the at least one first block and the at least one second block comprise at least one monomer chosen from (meth)acrylic acid esters and optionally at least one monomer chosen from (meth)acrylic acid, and their mixtures.

45. The cosmetic composition according to claim 8, wherein each of the at least one first block and the at least one second block results, in all, from at least one monomer chosen from (meth)acrylic acid esters and at least one monomer chosen from (meth)acrylic acid, and their mixtures.

46. The cosmetic composition according to claim 1, wherein the at least one first block and the at least one second block are such that the difference between the glass transition temperatures (Tg) of the at least one first block and the at least one second block is greater than 10° C.

47. The cosmetic composition according to claim 46, wherein the at least one first block and the at least one second block are such that the difference between the glass transition temperatures (Tg) of the at least one first block and the at least one second block is greater than 40° C.

48. The cosmetic composition according to claim 1, wherein the intermediate block has a glass transition temperature between the glass transition temperature of the at least one first block and the glass transition temperature of the at least one second block.

49. The cosmetic composition according to claim 1, wherein the at least one block polymer has a polydispersity index of greater than or equal to 2.5.

50. The cosmetic composition according to claim 49, wherein the at least one block polymer has a polydispersity index of from 2.8 to 6.

51. The cosmetic composition according to claim 1, wherein the at least one block polymer has a weight-average mass (Mw) of less than or equal to 300,000.

52. The cosmetic composition according to claim 51, wherein the at least one block polymer has a weight-average mass ranging from 45,000 to 150,000.

53. The cosmetic composition according to claim 1, wherein the at least one block polymer has a number-average mass (Mn) of less than or equal to 70,000.

54. The cosmetic composition according to claim 53, wherein the at least one block polymer has a number-average mass ranging from 12,000 to 50,000.

55. The cosmetic composition according to claim 1, wherein the at least one block polymer is insoluble, at an active material content of at least 1% by weight, in water or in a mixture of water and of linear or branched lower monoalcohols having from 2 to 5 carbon atoms, without modification of pH, at ambient temperature (25° C.).

56. The cosmetic composition according to claim 1, wherein the at least one block polymer is present in an amount ranging from 0.1% to 90% by weight relative to the total weight of the composition.

57. The cosmetic composition according to claim 56, wherein the at least one block polymer is present in an amount ranging from 0.5% to 30% by weight relative to the total weight of the composition.

58. The cosmetic composition according to claim 1, wherein the at least one plasticizer is a compound having a solubility parameter $\delta_h$ ranging from 5.5 to 11 $(J/cm^3)^{1/2}$.

59. The cosmetic composition according to claim 58, wherein the at least one plasticizer is a compound having a solubility parameter $\delta_h$ ranging from 8 to 10 $(J/cm^3)^{1/2}$.

60. The cosmetic composition according to claim 1, wherein the at least one plasticizer is a compound having a solubility parameter $\delta_p$ ranging from 1.5 to 4.5 $(J/cm^3)^{1/2}$.

61. The cosmetic composition according to claim 60, wherein the at least one plasticizer is a compound having a solubility parameter $\delta_p$ ranging from 2 to 3 $(J/cm^3)^{1/2}$.

62. The cosmetic composition according to claim 1, wherein the at least one plasticizer has a molecular mass of less than or equal to 5,000 g/mol.

63. The cosmetic composition according to claim 62, wherein the at least one plasticizer has a molecular mass of greater than or equal to 100 g/mol.

64. The cosmetic composition according to claim 1, wherein the at least one plasticizer is an ester.

65. The cosmetic composition according to claim 1, wherein the at least one plasticizer is chosen from esters of at least one carboxylic acid comprising 1 to 7 carbon atoms and at least one polyol comprising at least 4 hydroxyl groups.

66. The cosmetic composition according to claim 65, wherein the at least one polyol is a monosaccharide.

67. The cosmetic composition according to claim 66, wherein the monosaccharide is a cyclized monosaccharide in the hemiacetal form.

68. The cosmetic composition according to claim 65, wherein the at least one polyol is chosen from D-ribose, D-xylose, L-arabinose, D-glucose, D-mannose, D-galactose, D-xylulose and D-fructose.

69. The cosmetic composition according to claim 68, wherein the at least one polyol is a mono- or polysaccharide comprising from 1 to 10 monosaccharide units.

70. The cosmetic composition according to claim 65, wherein the at least one polyol is a mono- or polysaccharide comprising one or two monosaccharide units.

71. The cosmetic composition according to claim 65, wherein the at least one polyol is chosen from erythritol, xylitol, sorbitol, glucose, sucrose, lactose and maltose.

72. The cosmetic composition according to claim 65, wherein the at least one polyol is sucrose.

73. The cosmetic composition according to claim 64, wherein the ester is a polyol esterified by at least two different monocarboxylic acids.

74. The cosmetic composition according to claim 65, wherein the at least one carboxylic acid is a $C_1$ to $C_7$ monocarboxylic acid.

75. The cosmetic composition according to claim 74, wherein the carboxylic acid is a $C_1$ to $C_5$ monocarboxylic acid.

76. The cosmetic composition according to claim 65, wherein the at least one carboxylic acid is chosen from acetic, n-propanoic, isopropanoic, n-butanoic, isobutanoic, tert-butanoic, n-pentanoic and benzoic acids.

77. The cosmetic composition according to claim 1, wherein the at least one plasticizer is a sucrose diacetate hexa(2-methylpropanoate).

78. The cosmetic composition according to claim 1, wherein the at least one plasticizer is chosen from esters of an aliphatic or aromatic polycarboxylic acid and of an aliphatic or aromatic alcohol comprising from 1 to 10 carbon atoms.

79. The cosmetic composition according to claim 78, wherein:
the aliphatic alcohol is chosen from alcohols $R_1OH$, wherein $R_1$ is chosen from methyl, ethyl, propyl, isopropyl, butyl, hexyl, ethylhexyl, decyl, isodecyl, benzyl and benzyl substituted by a $C_1$ to $C_3$ alkyl, and their mixtures;
the aliphatic or aromatic polycarboxylic acid comprises from 3 to 12 carbon atoms.

80. The cosmetic composition according to claim 78, wherein the aliphatic or aromatic polycarboxylic acid is chosen from dicarboxylic acids and tricarboxylic acids.

81. The cosmetic composition according to claim 78, wherein the polycarboxylic acid is a dicarboxylic acid chosen from succinic acid, adipic acid, sebacic acid and phthalic acid.

82. The cosmetic composition according to claim 78, wherein the polycarboxylic acid is an acid of formula:

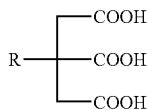

in which R is chosen from —H, —OH and —OCOR' groups in which R' is a $C_1$ to $C_6$ alkyl group.

83. The cosmetic composition according to claim 78, wherein the polycarboxylic acid is chosen from acetylcitric acid, butyroylcitric acid and citric acid.

84. The cosmetic composition according to claim 78, wherein the ester is chosen from tributyl acetylcitrate, triethyl acetylcitrate, triethylhexyl acetylcitrate, trihexyl acetylcitrate, trihexyl butyroylcitrate, triisodecyl citrate, triisopropyl citrate, tributyl citrate and tri(2-ethylhexyl) citrate, dibutyl adipate, di(2-ethylhexyl) adipate, dibutyl sebacate, di(2-ethylhexyl) sebacate, diethyl sebacate, diisopropyl sebacate, di(2-ethylhexyl) succinate, diethyl succinate, butyl benzyl phthalate, dibutyl phthalate, diethylhexyl phthalate, diethyl phthalate and dimethyl phthalate.

85. The cosmetic composition according to claim 58, wherein the at least one plasticizer does not comprise any polar group with the exception of the ester group wherein said polar group is defined as an ionic or non-ionic polar group chosen from —COOH, —OH, ethylene oxide, propylene oxide, —$PO_4$, —NHR and —$NR_1R_2$ group wherein $R_1$ and $R_2$ are chosen, independently, from $C_1$ to $C_{20}$ alkyl radicals and $C_1$ to $C_{20}$ alkoxy radicals which can be linear, branched or cyclic.

86. The cosmetic composition according to claim 85, wherein the at least one plasticizer does not comprise any hydroxyl group.

87. The cosmetic composition according to claim 1, wherein the at least one plasticizer is present in an amount ranging from 0.1% to 25% by weight relative to the total weight of the composition.

88. The cosmetic composition according to claim 87, wherein the at least one plasticizer is present in an amount ranging from 3% to 15% by weight relative to the total weight of the composition.

89. The cosmetic composition according to claim 1, wherein the at least one block polymer and the at least one plasticizer are present in an amount such that the ratio by weight of the block polymer to the plasticizer ranges from 0.5 to 100.

90. The cosmetic composition according to claim 89, wherein the at least one block polymer and the at least one plasticizer are present in an amount such that the ratio by weight of the block polymer to the plasticizer ranges from 1 to 5.

91. The cosmetic composition according to claim 1, further comprising at least one volatile oil.

92. The cosmetic composition according to claim 1, further comprising at least one volatile oil chosen from octamethylcyclotetrasiloxane, decamethylcyclopentasiloxane, dodecamethylcyclohexasiloxane, heptamethylhexyltrisiloxane, heptamethyloctyltrisiloxane, octamethyltrisiloxane, decamethyltetrasiloxane, isododecane, isodecane and isohexadecane.

93. The cosmetic composition according to claim 91, wherein the at least one volatile oil is present in an amount ranging from 0.1% to 90% by weight relative to the total weight of the composition.

94. The cosmetic composition according to claim 91, wherein the at least one volatile oil is present in an amount ranging from 5% to 50% by weight relative to the total weight of the composition.

95. The cosmetic composition according to claim 1, further comprising at least one nonvolatile oil.

96. The cosmetic composition according to claim 95, wherein the at least one nonvolatile oil is chosen from nonvolatile hydrocarbon oils and nonvolatile silicone oils.

97. The cosmetic composition according to claim 1, wherein the at least one nonvolatile oil is present in an amount ranging from 0.1% to 20% by weight relative to the total weight of the composition.

98. The cosmetic composition according to claim 97, wherein the at least one nonvolatile oil is present in an amount ranging from 1% to 10% by weight relative to the total weight of the composition.

99. The cosmetic composition according to claim 1, further comprising at least one fatty substance which is solid at ambient temperature chosen from waxes, pasty fatty substances, gums and their mixtures.

100. The cosmetic composition according to claim 1, further comprising from 0.1 to 50% by weight of waxes relative to the total weight of the composition.

101. The cosmetic composition according to claim 100, comprising from 1 to 30% by weight of waxes relative to the total weight of the composition.

102. The cosmetic composition according to claim 1, further comprising a coloring material.

103. The cosmetic composition according to claim 1, further comprising at least one cosmetic ingredient chosen from additional film-forming polymers, vitamins, thickeners, trace elements, softeners, sequestering agents, fragrances, basifying or acidifying agents, preservatives, sunscreen agents, surfactants, antioxidants, agents for combating hair loss, antidandruff agents, propellants and their mixtures.

104. The cosmetic composition according to claim 1, wherein the cosmetic composition is provided in the form of a suspension, dispersion, solution, gel, emulsion, cream, foam, dispersion of vesicles, two-phase or multiphase lotion, spray, and powder.

105. The cosmetic composition according to claim 1, wherein the cosmetic composition is provided in the form of a paste chosen from a soft paste and anhydrous paste.

106. The cosmetic composition according to claim 1, wherein the cosmetic composition is provided in anhydrous form.

107. The cosmetic composition according to claim 1, wherein the cosmetic composition is a product for making up or caring for keratinous substances.

108. The cosmetic composition according to claim 1, wherein the cosmetic composition is a product for making up the lips.

109. A cosmetic composition comprising, in a cosmetically acceptable organic liquid medium, at least one block polymer and at least one plasticizer, wherein:
the at least one block polymer has a polydispersity index I of greater than 2 and is a film-forming linear ethylenic polymer;
the at least one plasticizer is a compound having a solubility parameter $\delta_h$ ranging from 5.5 to 11 $(J/cm^3)^{1/2}$; and
the at least one block polymer comprises at least one first block and at least one second block having different glass transition temperatures (Tg), wherein the at least one first block and the at least one second block are connected to one another via an intermediate block comprising at least one constituent monomer of the at least one first block and at least one constituent monomer of the at least one second block, and further wherein said intermediate block is a random copolymer block.

110. A multi-compartment kit comprising:
a) a container delimiting at least one compartment, the container being closed by a closing element; and
b) a composition positioned inside the at least one compartment, wherein the composition comprises, in a cosmetically acceptable organic liquid medium, at least one block polymer and at least one plasticizer, wherein:
the at least one block polymer has a polydispersity index I of greater than 2 and is a film-forming linear ethylenic polymer devoid of styrene;
the at least one plasticizer is a compound, the nature and the amount of which allow the composition to form a film having a hardness of less than or equal to 35 seconds, the hardness of the film being measured using a Persoz pendulum according to the December 1991 version of Standard NF-T-30-016; and
the at least one block polymer comprises at least one first block and at least one second block having different glass transition temperatures (Tg), wherein the at least one first block and the at least one second block are connected to one another via an intermediate block comprising at least one constituent monomer of the at least one first block and at least one constituent monomer of the at least one second block, and further wherein said intermediate block is a random copolymer block.

111. The cosmetic assembly according to claim 110, wherein the container is formed, at least partially, of at least one thermoplastic material.

112. The cosmetic assembly according to claim 110, wherein the container is formed, at least partially, of at least one nonthermoplastic material.

113. The cosmetic assembly according to claim 110, wherein, in the closed position of the container, the closing element is screwed to the container.

114. The cosmetic assembly according to claim 110, wherein, in the closed position of the container, the closing element is coupled to the container in a manner other than by screwing.

115. The cosmetic assembly according to claim 110, wherein, in the closed position of the container, the closing element is coupled to the container by snapping, adhesive bonding, and/or welding.

116. The cosmetic assembly according to claim 110, wherein the composition is substantially at atmospheric pressure inside the compartment.

117. The cosmetic assembly according to claim 110, wherein the composition is pressurized inside the container.

118. A cosmetic process for making up or caring for keratinous substances, comprising:
applying to the keratinous substances a cosmetic composition;
the composition comprising, in a cosmetically acceptable organic liquid medium, at least one block polymer and at least one plasticizer, wherein:
the at least one block polymer has a polydispersity index I of greater than 2 and is a film-forming linear ethylenic polymer devoid of styrene;
the at least one plasticizer is a compound, the nature and the amount of which allow the cosmetic composition to form a film having a hardness of less than or equal to 35 seconds, the hardness of the film being measured using a Persoz pendulum according to the December 1991 version of Standard NF-T-30-016; and
the at least one block polymer comprises at least one first block and at least one second block having different glass transition temperatures (Tg), wherein the at least one first block and the at least one second block are connected to one another via an intermediate block comprising at least one constituent monomer of the at least one first block and at least one constituent monomer of the at least one second block, and further wherein said intermediate block is a random copolymer block.

119. A process for producing a deposited layer on keratinous substances which is flexible and/or comfortable over time, said process comprising:
applying to said keratinous substances a composition comprising, in a cosmetically acceptable organic liquid medium, at least one block polymer and at least one plasticizer, wherein:
the at least one block polymer has a polydispersity index I of greater than 2 and is a film-forming linear ethylenic polymer devoid of styrene;
the at least one plasticizer is a compound, the nature and the amount of which allow the cosmetic composition to form a film having a hardness of less than or equal to 35 seconds, the hardness of the film being measured using a Persoz pendulum according to the December 1991 version of Standard NF-T-30-016; and
the at least one block polymer comprises at least one first block and at least one second block having different glass transition temperatures (Tg), wherein the at least one first block and the at least one second block are connected to one another via an intermediate block comprising at least one constituent monomer of the at least one first block and at least one constituent monomer of the at least one second block, and further wherein said intermediate block is a random copolymer block.

120. A process for producing a deposited layer on keratinous substances which is flexible and/or comfortable over time, said process comprising:
applying to said keratinous substances a cosmetic composition comprising, in a cosmetically acceptable organic liquid medium, at least one film-forming linear ethylenic block polymer having a polydispersity index I of greater than 2;

at least one plasticizer having a solubility parameter $\delta_h$ ranging from 5.5 to 11 $(J/cm^3)^{1/2}$; and the at least one block polymer comprises at least one first block and at least one second block having different glass transition temperatures (Tg), wherein the at least one first block and the at least one second block are connected to one another via an intermediate block comprising at least one constituent monomer of the at least one first block and at least one constituent monomer of the at least one second block, and further wherein said intermediate block is a random copolymer block.

* * * * *